United States Patent
Smithwick et al.

(10) Patent No.: US 6,845,190 B1
(45) Date of Patent: Jan. 18, 2005

(54) CONTROL OF AN OPTICAL FIBER SCANNER

(75) Inventors: Quinn Y. J. Smithwick, Bothell, WA (US); Eric J. Seibel, Seattle, WA (US); Mark Fauver, Seattle, WA (US)

(73) Assignee: University of Washington, Seattle, WA (US)

( * ) Notice: Subject to any disclaimer, the term of this patent is extended or adjusted under 35 U.S.C. 154(b) by 266 days.

(21) Appl. No.: 10/305,914

(22) Filed: Nov. 26, 2002

Related U.S. Application Data

(63) Continuation-in-part of application No. 09/994,377, filed on Nov. 26, 2001.
(60) Provisional application No. 60/333,421, filed on Nov. 26, 2001, and provisional application No. 60/253,445, filed on Nov. 27, 2000.

(51) Int. Cl.$^7$ .............................................. G02B 6/26
(52) U.S. Cl. ........................ 385/25; 385/115; 385/116; 385/1; 385/4; 385/11; 385/12; 385/147
(58) Field of Search ................................ 385/116, 115, 385/1, 2, 3, 4, 11, 12, 14, 25, 27, 147, 901

(56) References Cited

U.S. PATENT DOCUMENTS

| | | | |
|---|---|---|---|
| 4,118,270 A | 10/1978 | Pan et al. ................... 156/659 |
| 4,265,699 A | 5/1981 | Ladany ....................... 156/657 |
| 4,410,235 A | 10/1983 | Klement et al. .......... 350/96.18 |
| 4,710,619 A | * 12/1987 | Haberl ....................... 250/206.3 |
| 4,782,228 A | * 11/1988 | Westell ......................... 250/236 |
| 4,824,195 A | 4/1989 | Khoe ....................... 350/96.18 |
| 5,037,174 A | 8/1991 | Thompson .................... 385/33 |
| 5,074,642 A | 12/1991 | Hicks .......................... 385/116 |
| 5,247,174 A | 9/1993 | Berman ....................... 250/235 |
| 5,272,330 A | 12/1993 | Betzig et al. ................ 250/216 |
| 5,360,968 A | * 11/1994 | Scott ........................... 235/454 |
| 5,394,500 A | 2/1995 | Marchman ................... 385/123 |
| 5,425,123 A | 6/1995 | Hicks .......................... 385/117 |
| 5,459,803 A | 10/1995 | Yamane et al. ............... 385/33 |
| 5,480,046 A | 1/1996 | Filas et al. ...................... 216/7 |
| 5,563,969 A | 10/1996 | Honmou ....................... 385/35 |
| 5,570,441 A | 10/1996 | Filas et al. .................... 385/43 |

(List continued on next page.)

FOREIGN PATENT DOCUMENTS

| | | | |
|---|---|---|---|
| EP | 1 142 529 A1 | 10/2001 | ............ A61B/1/00 |
| JP | 2001174744 A2 | 6/2001 | ........... G02B/26/10 |

OTHER PUBLICATIONS

Yamada, Jun–Ichi et al. Oct. 1980. Characteristics of a Hemispherical Microlens for Coupling Between a Semiconductor Laser and Single–Mode Fiber. *IEEE J. Quant. Electron.* QE–16:10:1067–1072.

Russo, Vera et al. Oct. 1, 1984. Lens–ended Fibers for Medical Applications: A New Fabrication Technique. *Appl. Opt.* 23:19:3277–3283.

(List continued on next page.)

*Primary Examiner*—Brian M. Healy
(74) *Attorney, Agent, or Firm*—Ronald M. Anderson

(57) ABSTRACT

Controls for an optical scanner, such as a single fiber scanning endoscope (SFSE) that includes a resonating optical fiber and a single photodetector to produce large field of view, high-resolution images. A nonlinear control scheme with feedback linearization is employed in one type of control to accurately produce a desired scan. Open loop and closed loops controllers are applied to the nonlinear optical scanner of the SFSE. A closed loop control (no model) uses either phase locked loop and PID controllers, or a dual-phase lock-in amplifier and two PIDs for each axis controlled. Other forms of the control that employ a model use a frequency space tracking control, an error space tracking control, feedback linearizing controls, an adaptive control, and a sliding mode control.

50 Claims, 9 Drawing Sheets

U.S. PATENT DOCUMENTS

| | | | | |
|---|---|---|---|---|
| 5,668,644 | A | * 9/1997 | Kuroiwa et al. | 358/480 |
| 5,703,979 | A | 12/1997 | Filas et al. | 385/43 |
| 5,727,098 | A | 3/1998 | Jacobson | 385/31 |
| 6,046,720 | A | 4/2000 | Melville et al. | 345/108 |
| 6,091,067 | A | 7/2000 | Drobot et al. | 250/234 |
| 6,161,035 | A | 12/2000 | Furusawa | 600/476 |
| 6,211,904 | B1 | 4/2001 | Adair et al. | 348/76 |
| 6,294,775 | B1 | 9/2001 | Seibel et al. | 250/208.1 |
| 6,327,493 | B1 | 12/2001 | Ozawa et al. | 600/476 |
| 2001/0030744 | A1 | * 10/2001 | Chang | 356/237.3 |
| 2002/0064341 | A1 | * 5/2002 | Fauver et al. | 385/25 |
| 2002/0131052 | A1 | * 9/2002 | Emery | 356/511 |
| 2003/0179428 | A1 | * 9/2003 | Suzuki et al. | 359/204 |

OTHER PUBLICATIONS

Lee, Kyung S. and Frank S. Barnes. Oct. 1, 1985. Microlenses on the End of Single–mode Optical Fibers for Laser Applications. *Appl. Opt*. 24:19:3134–3139.

Barnard, Chris W. and John W. Y. Lit. May 20, 1991. Single–mode Fiber Microlens with Controllable Spot Size. Appl. Opt. 30:15:1958–1962.

Barnard, Chris W. and John W. Y. Lit. Apr. 20, 1993. Mode Transforming Properties of Tapered Single–mode Fiber Microlens. *Appl. Opt*. 30:15:1958–1962.

* cited by examiner

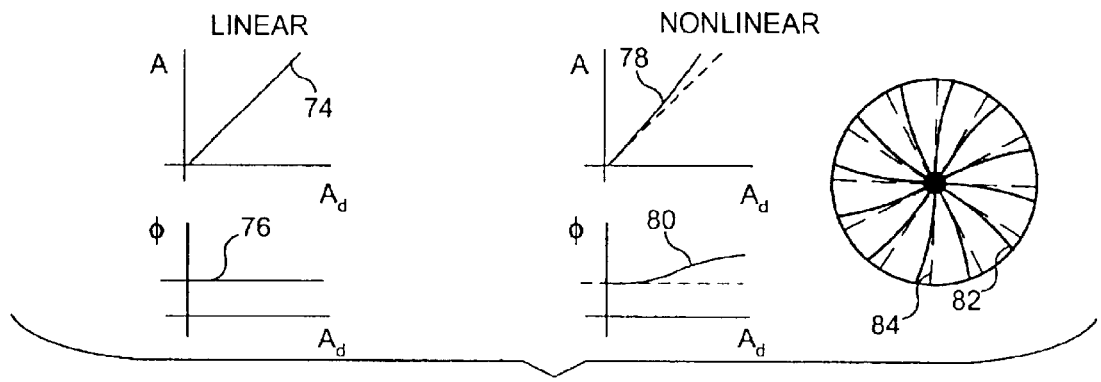
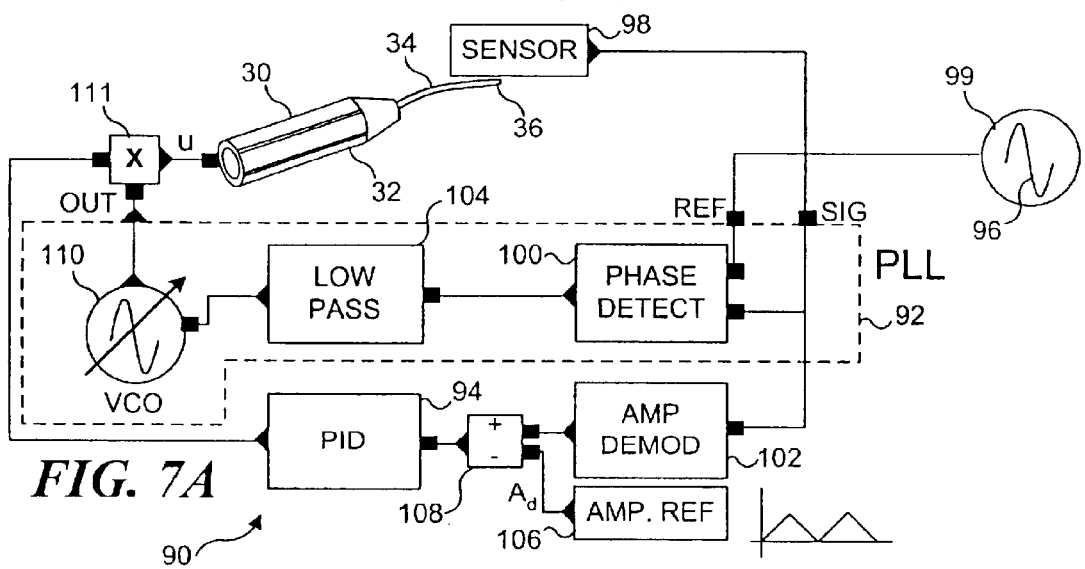
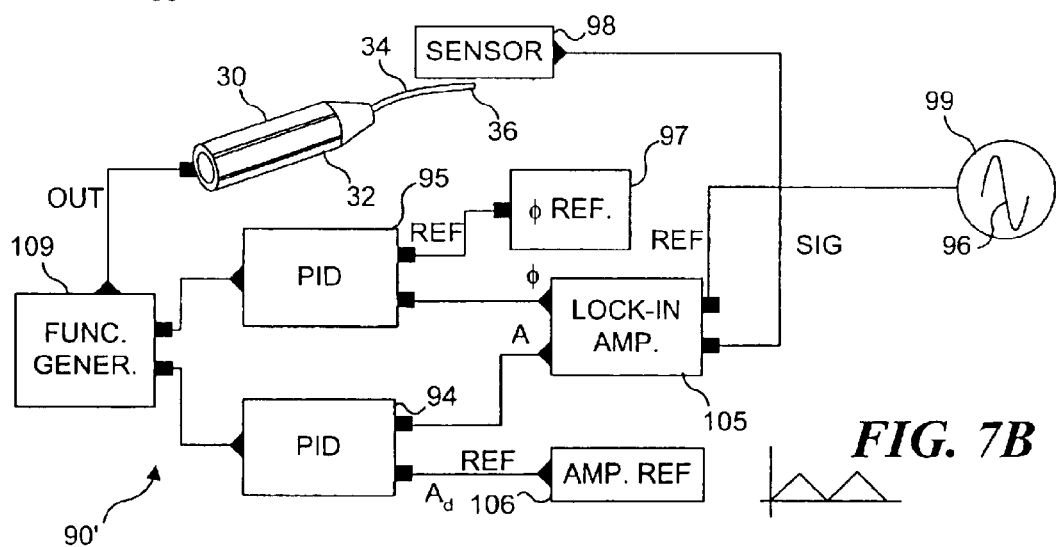

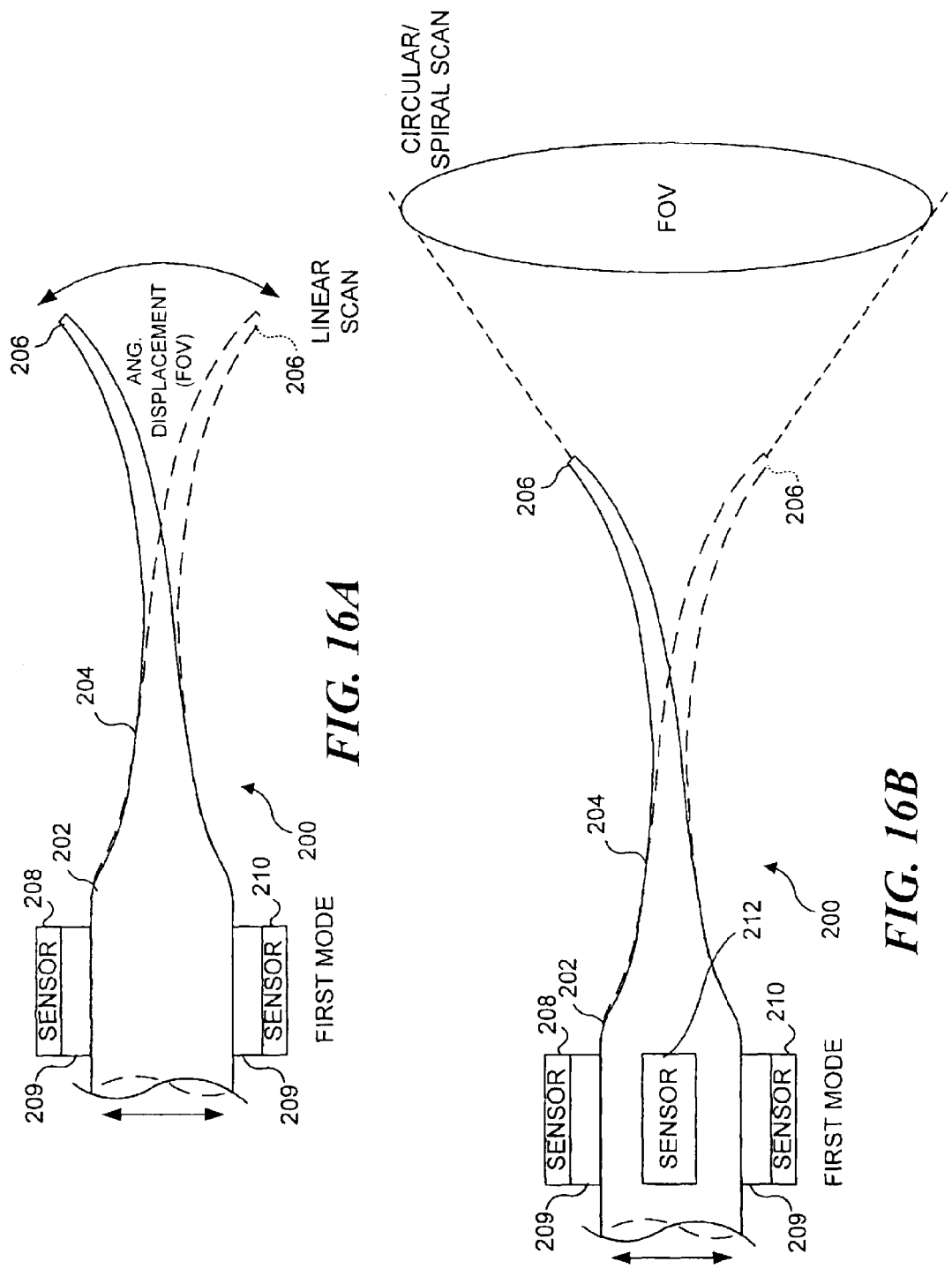

CONTROL OF AN OPTICAL FIBER SCANNER

RELATED APPLICATIONS

This application is based upon U.S. Provisional Patent Application Ser. No. 60/333,421, filed Nov. 26, 2001, the benefit of the filing date of which is hereby claimed under 35 U.S.C. § 119(e). This application is also a continuation-in-part of U.S. Pat. Application Ser. No. 09/994,377, pending, filed Nov. 26, 2001 (based upon U.S. Provisional Patent Application Ser. No. 60/253,445, filed Nov. 27, 2000), the benefit of the filing dates of which is hereby claimed under 35 U.S.C. § 120 and 35 U.S.C. § 119(e).

FIELD OF THE INVENTION

The present invention generally relates to controls for an optical scanner, and more specifically, to controls for a resonant optical scanner that is used either for image acquisition or display of an image, wherein the controls determine the movement of a cantilevered distal tip of the optical fiber relative to an adjacent surface.

BACKGROUND OF THE INVENTION

The combination of an optical fiber's low mass, low moment of inertia, and light damping results in large amplitudes or large angular deflections at its tip when excited into resonance. Small movements of the actuator at the base of an optical fiber (base excitation) or weak forces produced by the actuator either along the length of the fiber or at its tip, efficiently result in large amplitudes or large angular deflections at the fiber's tip. When driven to move at resonance or near resonance, an optical fiber scanner can be used for image display and acquisition, as well as the basis of several fiber optic sensors, e.g. media density, temperature, or proximity to a surface (atomic force microscopy).

Most optical scanning applications use a moving mirror, either rotating or oscillating. A laser beam is often projected onto the moving mirror to scan the beam across a specified linear or two-dimensional (2D) (raster) pattern at a frequency that is sufficient for the particular application. For optical displays, the field of view (FOV) is determined by the scanning amplitude and the particular optical design. There is a minimum frequency (rate) at which scanning displays need to be refreshed, which is determined by the human perception of flicker from a scanned display. For ubiquitous raster scanning displays, such as cathode ray tubes (CRTs) used in televisions and computer monitors, the display refresh rate is typically 30 to 60 Hz. Although a CRT employs an electron beam for scanning an electro-optical display screen, the same requirements for scan frequency and amplitude (that determine the FOV) generally apply for all types of scanning displays. Thus, for a super video graphics array (SVGA) display having a CRT resolution of 800×600 pixels, the minimum horizontal scan rates are 40 kHz for unidirectional and 18 kHz for bi-directional scanning.

Combining both high resolution (>100,000 pixels) and wide FOV (>30°) in a single display is a difficult technical challenge, limiting the application of optical scanning for small size, low cost optical scanners that have both high resolution and wide FOV. To date, a mirror-based resonant scanner fabricated as a micro-electromechanical systems (MEMS) device has yet to be demonstrated as a viable method for manufacturing low cost optical scanners for visual displays of wide FOV and at video scan rates.

There is a growing market for micro-optical displays as well as small optical sensors, optical switches, and scanning image acquisition systems. For example, a low cost micro-optical scanner is essential for spectacle-mounted, retinal light scanning displays and micro-displays that may be embedded in future cellular telephones. Moreover, there is a commercial need for low cost, large-scale (panoramic) optical displays, because larger CRT displays are uneconomical in energy and space. There is also a growing market for optical sensing and switching, especially in conjunction with fiber-optic sensing and communication applications. Finally, the lack of low cost micro-optical scanners with a wide FOV has been the most significant barrier for reducing the size of scanning image acquisition systems for use in surveillance, industrial inspection and repair, machine and robotic vision systems, micro-barcode scanners, and minimally-invasive medical imaging, e.g., a flexible single fiber scanning endoscope (SFSE).

To address some of the problems noted above with mirror-based scanners, optical fiber scanners have been developed that are relatively compact and usable for either image acquisition or image display. The scanning optical fiber is preferably actuated to move either in one dimension or in two dimensions using, for example, piezoelectric bimorph or tube actuators. By tapering a distal end of the optical fiber to a relatively small size, large FOVs have been obtained as the optical fiber is driven to move relatively to a surface. When used for image acquisition, one or more laser light sources coupled to the proximal end of the optical fiber provide light that is emitted from the distal tip as it scans a surface. The actuator(s) can cause the distal tip to scan the surface in a linear motion or a space-filling motion, such as a raster pattern, a spiral pattern, a propeller pattern, various Lissajous scanning patterns, and in other desired patterns. One or more photodetectors disposed adjacent to the distal tip (or elsewhere, if other optical fibers convey the reflected light to remote photo detectors) respond to light reflected from the surface, producing a signal that can be processed or employed to produce an image of the surface being scanned. When used to display an image, a modulated light source responds to an input signal producing light that is then emitted by the distal tip of the scanning optical fiber as it scans either an adjacent surface, or a user's eye (i.e., retina). The modulated light emitted is applied to create a pixilated array of light spots on the surface or on the retina of a user's eye, forming an image. However, these and various other applications of a scanning optical fiber require control of the actuators employed to cause the distal tip of the optical fiber to move in the desired scanning pattern. Various problems must be addressed by the control scheme employed for this purpose.

For example, although spiral pattern scans can be implemented efficiently with a very compact scanning optical fiber, it has been found that a spiral pattern of light emitted by a scanning optical fiber is subject to distortion that adversely affects the spiral pattern. In the quest to increase the performance of a SFSE and scanning optical fibers used in other applications, simulations have been run to discover the source of the distortions or breakdown of the spiral scan pattern. These simulations, which are based upon a nonlinear model of a piezo-tube driven base excited resonating fiber, show that the interactions of low damping, transient response after discontinuities, and nonlinear amplitude and phase responses are the major sources of distortion.

Because a resonant amplification occurs only in a small frequency range around the resonant frequency of an optical fiber, the optical fiber acts as a band-pass filter (amplifier)

between an actuator input and the resulting motion of the optical fiber (i.e., its scanning motion). Other that at the fundamental frequency, many of the frequency components of complex scan patterns (e.g., square or triangle waves) are not sufficiently amplified to provide the corresponding complex motion. As a result, the optical fiber scanners are usually used to produce nearly sinusoidal scans, typically at a constant amplitude and phase, with respect to the drive signal applied as an actuator input.

The amplitude and phase response of an optical fiber scan may vary greatly between scanners and within the same scanner over time, due to differences or changes in the scanner resonant properties. Between scanners, differences in resonant properties are due to manufacturing variability either in the length of the fiber, quality of actuator/fiber coupling, or actuator efficiency. A single scanner's resonant properties may change due to environmental effects (temperature changes) or aging (fiber cracking, actuator/fiber coupling deterioration). Generally, it is preferable to achieve a consistent behavior between scanners, and within the same scanner over time.

The low mass and light damping of the fiber, while essential for large resonant amplification, also allow disturbances to persist for long periods of time. Also, optical fibers undergoing large deflections exhibit nonlinear behavior. This behavior includes amplitude and phase shifts in the output that are dependent on the amplitude of the input, cross-coupling of the optical fiber vibration axes, and possible bi-stable output amplitude. This nonlinear behavior produces undesirable scan distortion or inconsistencies.

Various control schemes can be employed in controlling the scanning motion of an optical fiber. In regard to the spiral scan problem noted above, it would be desirable to remove the distortion and make the scan pattern robust to scanner variations. An appropriate controller should be capable of asymptotically tracking the spiral scan pattern with minimal error and maximum robustness. To achieve acceptable results in an appropriate control for achieving a spiral scan and other desired scanning patterns, an appropriate control approach must be developed.

SUMMARY OF THE INVENTION

The present invention is thus directed to developing controllers for an optical scanner. The disclosed preferred embodiments are directed to controllers for a cantilevered light guide or resonant optical fiber. As used herein, the term "light guide" is intended to encompass wave guides, optical fibers, and other structures that convey light along a desired path. Also, as used herein and in the claims that follow, the term "optical scanner" is intended to refer to a vibrating device that projects, directs, or redirects light in a desired direction and includes without limitation, vibrating mirrors and light guides.

A first aspect of the present invention is directed to a controller for an optical scanner that is driven to move in a desired pattern. The controller includes a reference phase signal source that produces a reference phase signal, and includes a phase control. The phase control is adapted to couple to a sensor to receive a position signal indicative of a position of a moving portion of the optical scanner. In addition, the phase control is coupled to the reference phase signal source to receive the reference phase signal and uses the reference phase signal and the position signal to produce a phase signal output. The controller has an amplitude reference source for producing an amplitude reference signal. An amplitude control is included and is adapted to couple to a sensor to receive the position signal. The amplitude control is also coupled to the amplitude reference signal source to receive the amplitude reference signal and produces an amplitude signal output in response to the position signal and the amplitude reference signal. The phase signal output and the amplitude signal output are then combined to control a drive signal used to drive the optical scanner to move in the desired pattern.

In one preferred embodiment, the phase control comprises a phase locked loop that varies the phase signal output so as to achieve a predefined relationship between the reference phase signal and the phase of the optical scanner. In this embodiment, the amplitude control comprises an amplitude demodulator that receives the position signal and determines an amplitude of the optical scanner's vibration. A proportional-integral-derivative feedback controller is coupled to the amplitude demodulator and produces the amplitude signal output so as to minimize an error in the amplitude of the optical scanner relative to the amplitude reference signal.

In another embodiment, the phase control comprises a lock-in amplifier that is coupled to the sensor and to the phase reference source and has a phase output and an amplitude output. The phase control also includes a first proportional-integral-derivative feedback controller that is coupled to the lock-in amplifier to receive the phase output and produces the phase signal output. The amplitude control in this other embodiment includes the lock-in amplifier, and a second proportional-integral-derivative feedback controller that is coupled to the lock-in amplifier to receive the amplitude output. The second proportional-integral-derivative feedback controller produces the amplitude signal output. The phase and amplitude output signals are combined to control the drive signal applied to actuate an optical scanner.

Yet another embodiment of the control includes a feedforward controller that employs a model of the optical scanner and is coupled to the reference signal source to receive at least one reference signal. The feedforward controller uses the model and at least one reference signal to determine a feedforward signal required to produce movement of the optical scanner in the desired pattern. A feedback controller that is adapted to couple to a sensor to receive a sensor signal indicative of movement by the optical scanner uses the sensor signal to determine a feedback signal appropriate to stabilize the controller and to reject disturbances of the optical fiber. The feedforward signal and the feedback signal are combined to control a drive signal used to drive the optical scanner to move in the desired pattern. The various embodiment of the controller can either be implemented with analog circuit components or digitally, using a computing device.

The controller may include one of several different sensors. One sensor includes a first photosensor that is responsive to stress-induced changes in a polarization vector of polarized light traveling through the optical scanner. The changes are caused by the bending of the portion of the optical scanner that is in motion. The first photosensor produces a sensor signal indicative of the position of the optical scanner relative to an axis.

Another embodiment of the sensor includes a plurality of sensor optical fibers disposed in an array about the optical scanner. The plurality of sensor optical fibers extend proximally of the portion of the optical scanner that is in motion. A partially reflective surface is disposed to reflect a portion of light emitted from the optical scanner back toward the plurality of sensor optical fibers. The portion of the light is conveyed through the plurality of sensor optical fibers. A 2D photodetector is disposed to receive the light conveyed through the plurality of sensor optical fibers and produces the signal indicative of the position of the optical scanner.

Still another aspect of the present invention is directed to a method for controlling an optical scanner. The method includes steps generally consistent with the functions of the elements comprising the controls discussed above. One preferred form of the method includes the step of producing the drive signal for driving the optical scanner in regard to a first axis and a second axis, where the second axis is generally orthogonal to the first axis. The drive signal produces a desired movement of the optical scanner about only one of the first and the second axes, but includes a component acting on the other of the first and the second axes so as to cancel out an unforced, undesired movement of the optical scanner caused by nonlinear coupling of the axes called whirl.

In addition, the feedback linearization is applied by using the model to estimate a nonlinear behavior of the optical scanner, and includes the step of providing an addition to the drive signal based upon the estimate to remove nonlinear behavior. Model parameters can be adjusted using an online parameter estimator, based upon a sensed position of the optical scanner and the actuator input to achieve robust cancellation.

Where the method uses a model, it further comprises the steps of approximating a continuous control input to the model so as to drive a tracking error in the motion of the optical scanner toward a zero value, and providing a discontinuous control input that is determined as a function of an upper bound on an uncertainty in the model, so that the optical scanner is controlled even though the model is incomplete.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 schematically illustrates the x-axis and y-axis scan signals that are input to a piezoelectric tube actuator to produce a spiral scan;

FIG. 6 illustrates graphs of non-linear amplitude and phase response versus drive amplitude, showing the resulting distortion;

FIG. 7A is a functional block diagram of a control that includes a phase lock loop (PLL) and a proportional, integral, derivative (PID) amplitude control for an optical fiber scanner;

FIG. 7B is a function block diagram of a control that includes a lock-in amplifier and two PID controls;

FIGS. 16A and 16B are schematic diagrams that respectively illustrate two sensors along the linear scan axis, and four sensors along the two orthogonal axes of a 2D scan pattern;

DESCRIPTION OF THE PREFERRED EMBODIMENTS

The present invention is directed to controlling cantilevered light guides used in a many different applications. While it should be clearly understood that the present invention is not limited to controlling just an optical fiber, an initial application of the present invention for that purpose provides a disclosure of several different embodiments of exemplary controls that are used in connection with controlling the drive signal applied to cause an optical fiber to move in a desired pattern at or near its resonance. However, it is not intended that the discussion of the present invention in connection with controlling the movement of an optical fiber in any way limit its application to that type of light guide.

A resonant optical fiber that is controlled by the present invention can be either tapered or non-tapered and can be driven in several scanning patterns, as appropriate for the application of the scanning optical fiber. The following discussion focuses on the control of resonant scanning optical fiber that is driven in a spiral pattern, since that pattern can be implemented using a cantilevered optical fiber drive system that is substantially more compact than, for example a raster pattern, and more efficient than patterns that repeatedly cross the same portion of a surface while completing a scan of the surface. An initial commercial application of this control will likely be in connection with a SFSE that can be inserted into a patient's body, and thus, much of the following discussion is directed to controlling the SFSE.

Figure 1:
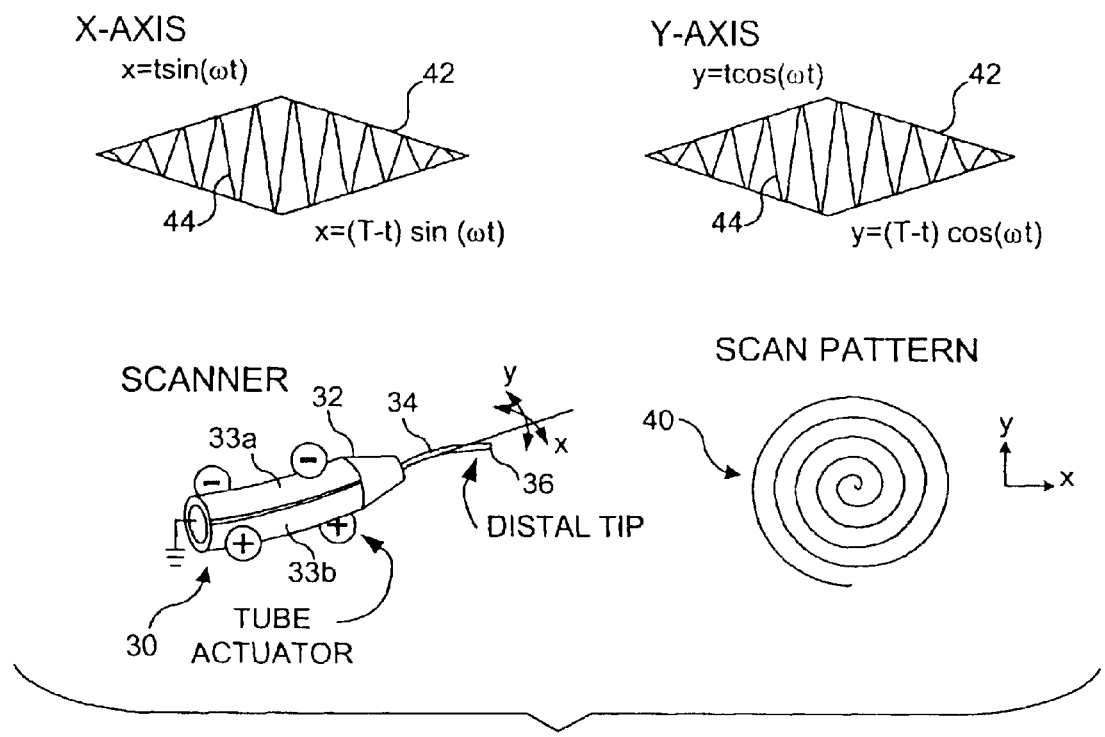

Specifically, a SFSE has been developed that is expected to provide the same image capabilities as current flexible fiber bundle endoscopes, but in a package no larger than 3 mm in diameter. Due to the inherent limitations of array acquisition with optical fibers used in flexible endoscopes, at bundle diameters less than 3 mm, the FOV or resolution of the optical fiber relay must be sacrificed. To achieve high resolution, wide field of view images from a smaller device, the SFSE uses a resonant optical fiber scanner 30, as shown in FIG. 1, to move a single light spot over a surface, and a single photodetector (not shown) to measure the intensity variation of the backscattered light from the spot on the illuminated surface. Using the collection of the positions of the spot of light and the intensity of the backscattered light from each of those positions, an intensity map of the surface can be made. The resolution of the device is independent of sensor size and only dependent on the spot size and sampling rate, and the FOV is determined by the scanning angle.

To produce the scan, opposite planar quadrants 33a, 33b of a piezoelectric tube actuator 32 are used to vibrate a cantilevered optical fiber 34 into resonance. The resonant behavior of the cantilevered optical fiber produces large deflections at a distal tip 36 of the optical fiber from small piezoelectric tube actuator movements at the base of the cantilever. Light emanating from the distal tip produces a large FOV scan, such as a spiral scan pattern 40. Various other space filling scan patterns besides the spiral scan pattern can be created by properly modulating the piezoelectric tube actuator drive signal, such as a raster scan and a propeller scan. However, to simplify the disclosure of the present invention, the following discussion will concentrate on control of the spiral scan.

Scan Patterns

The simplest 2D scan patterns are created by using synchronized horizontal and vertical sinusoidal vibrations to produce a 1:1 Lissajous pattern. A circular scan results when the horizontal and vertical resonant vibrations are of the same frequency and equal amplitude, but 90° out of phase. To create a spiral scan, the amplitudes are modulated in a triangle pattern 42, while the phases are kept constant. See FIG. 1. The applied signal can be described as a triangle amplitude modulated sine wave 44, with the carrier being the resonant frequency, and the triangle modulation being applied to the amplitude of the sine wave. Each half cycle of the triangle modulation is a frame. A sinusoidal modulation for each frame is another technique that does not have a discontinuity in slope; however, the triangular pattern is an excellent choice for comparing different optical fiber scanning control methods.

In the prior art, 2D space-filling resonant scans from a single actuator are produced using an "offset frequency" x:y Lissajous pattern. The resonant frequencies in the two axes are required to be different. The resultant x:y Lissajous pattern is inefficient, and typically requires custom fibers.

Alternatively, a 2D pattern can be produced using a symmetric fiber with equal resonant frequencies in both axes. If the horizontal axes produce a constant amplitude sine wave, and the vertical axes produce a cosine wave of the same frequency and amplitude (but with a 90° phase difference), a circle results. This circular pattern is a 1:1 Lissajous pattern, but this pattern does not scan over an area, i.e., it is not space filling.

To produce a space filling scan from a circular scan, the circular scan's amplitude can be progressively decreased and increased, yielding a spiral scan. This spiral scan is an amplitude modulated 1:1 Lissajous pattern. For an evenly spaced spiral, the horizontal vibration can be a triangle amplitude modulated sine wave, and the vertical vibration can be a triangle amplitude modulated cosine wave. If the amplitude modulation does not periodically go to zero, the spiral scan becomes a toroidal scan. Alternatively, if the drive signal applied to drive a scan along the horizontal axis is a constant amplitude sine wave, and in regard to the vertical axes, the drive signal is also a sine wave of the same frequency and amplitude (with no phase difference), a 45° line results. Again, this line is not a space-filling scan. To produce, a space-filling scan, it is necessary to modulate the amplitudes of the signal for each axis. If the amplitudes of the horizontal and vertical components of the drive signal vary, but maintain a relation such that the sum of the squares of the components remains constant, the line scan appears to rotate, and the resulting scan pattern is called a "propeller scan." To produce a scan with a constant angular velocity (constant spin speed), the horizontal vibration can be a cosine modulated sine wave, and the vertical vibration can be a sine wave modulated sine wave.

If the horizontal component is a sine wave and the vertical component is a cosine wave, a circle results. Modulating the amplitudes creates a spiral scan. If the horizontal component is a sine wave and the vertical component is also a sine wave, a skewed 45° line results. If the amplitudes are modulated, a propeller scan results. If the horizontal component is a sine wave, and the vertical component is a sine wave, but with a phase shift somewhere between 90° (a cosine wave), and 0° (a sine wave), a skewed oval results. If the amplitudes remain constant and the phases are varied, a result similar to an x:y Lissajous pattern results, which is a phase-modulated sine wave.

The use of amplitude modulated scans gives a resonant optical fiber the ability to produce 2D scan patterns from a single small package, compared to a 1D resonant scan plus a galvo-mirror that is typically used in conventional 2D scanners and provides a more efficient, even scan pattern than a 2D scanned x:y Lissajous scan pattern produced by a rectangular cross section optical fiber.

Open Loop Control

In current prototypes of the SFSE, the piezoelectric tube actuators are driven with a signal having a shape expected to produce a desired output. A sync pulse starts the data acquisition for each frame of data acquired by the SFSE. The output scan is a scaled and distorted version of the drive waveform, with a phase shift in the carrier and the modulation waveforms. The phase of the carrier and modulation waves relative to the sync pulse and the modulation amplitude are adjusted manually until a coherent image is created. Indeed, if the SFSE is run "open loop," the frequency, phase, and amplitude of the scanner are all typically adjusted manually.

Figure 2A:
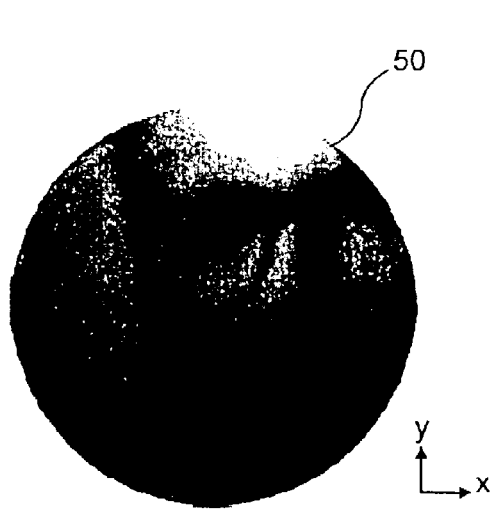
FIG. 2A is an exemplary low-frame rate image produced from a optical fiber scanner.

An exemplary image 50 in FIG. 2A illustrates the result produced by using 125 scan rings with 200 samples per ring. These frame rates are for a particular optical fiber scanner used to acquire the image in FIG. 2A. Changes in the optical fiber scanner that is used, including the piezoelectric tube actuator and the optical fiber coupling, optical fiber type, optical fiber geometry, and resonant frequency may change the behavior of the optical scanner, but the general characteristics of a 2D resonant fiber scanning system will generally remain the same.

To understand the causes of the distortion and the toroidal scan behavior that occur as the frame rate increases when an optical fiber is driven to produce a spiral scan pattern, the dynamics of 2D resonant fiber scanning system must be examined. This objective was accomplished by creating a dynamic model of the scanning system and running numerical simulations to gain insight into the problem.

In order to increase the performance of an optical fiber scanner in producing a spiral scan, various control schemes were tested. The goal of these control schemes is to force the system to perfectly track the triangle modulated sine wave (shown in FIG. 1), thereby removing distortion and the toroidal scan behavior. The results of these tests are also applicable to achieving other scanning patterns, both 1D and 2D. An additional feature desired of an optical fiber scanner controller is robustness in handling the inevitable variations in the scanner system due to manufacturing variability and/or environmental effects, i.e., to achieve an ideal scanning controller that ensures all light guide scanners that it controls behave the same, independent of slight differences in construction or operating conditions.

Open Loop Simulation

Figure 3:
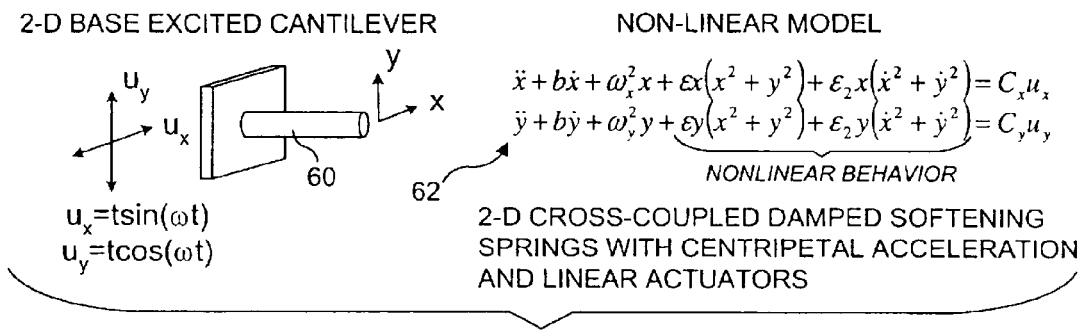
FIG. 3 illustrates the equations for a non-linear model of a 2D excited optical fiber scanner.

To create the dynamic model used in some of the control schemes, an optical fiber scanner was considered as a resonating base, excited cantilever. Because the optical fiber is driven through large displacements, nonlinear optical fiber dynamics are expected to dominate. Using nonlinear continuum equations (known in the art) for a base excited cantilever 60, approximate differential equations 62 can be developed for the scanning system's behavior near resonance, as shown in FIG. 3. The model is in the same form as a 2D, cross-coupled damped oscillator with softening springs, centripetal acceleration, and a linear actuator. The coefficients for the differential equations shown in FIG. 3 are empirically determined.

Figure 2B:
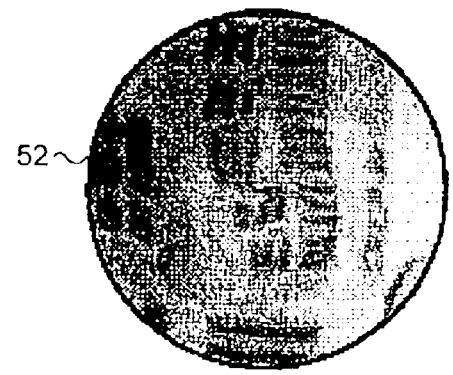
FIG. 2B is an exemplary open loop (no controller feedback error correction) image, using a spiral 500 Hz resonant scan, with 1 Hz modulation.
Figure 2C:
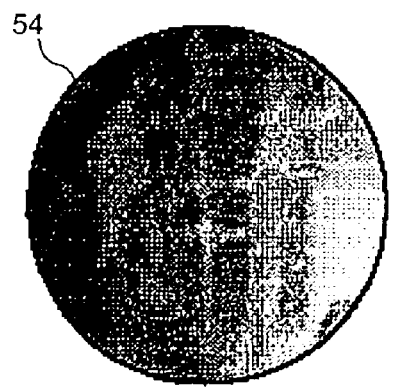
FIG. 2C is an exemplary controlled acquired image using a controller with no feedback linearization, a spiral 500 Hz resonant scan, with 1 Hz modulation, at a 20 kHz loop rate.
Figure 4:
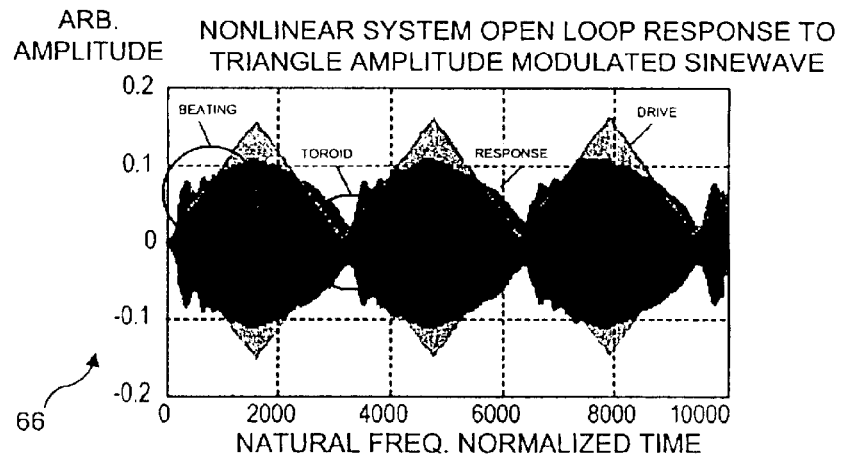
FIG. 4 is a graph of amplitude versus a reference and response for an open loop simulation.

In FIG. 4, results 66 using a nonlinear system model show that a spiral scan's amplitude modulation will not be linear, but will instead decay into and out of a triangle envelope, creating distortion in the image. An exemplary image 52 in FIG. 2B illustrates the distortion that results in an open loop scanning controller during a spiral scan. This problem is mainly due to the cantilevered optical fiber's low damping. There is also noticeable beating evident in the scan pattern after each discontinuity. In contrast, a corresponding exemplary image 54 is shown in FIG. 2C, for an optical fiber scanner controlled with the present invention.

Figure 5:
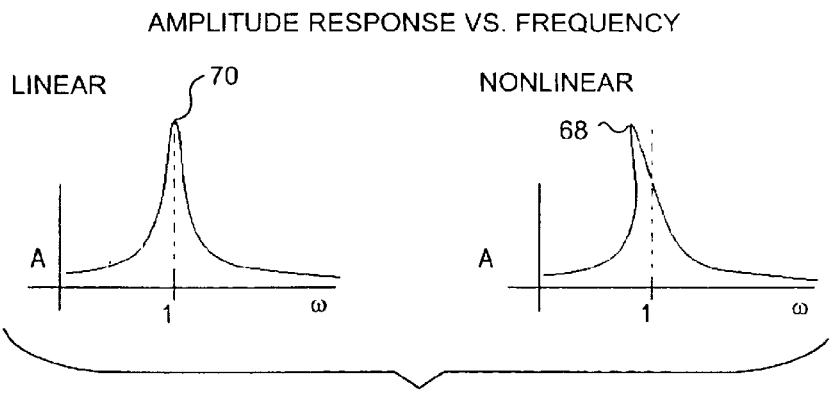
FIG. 5 shows two graphs showing a linear and a non-linear amplitude response versus frequency for an optical fiber scanner.

At the modulation discontinuities, the optical fiber will be excited, creating transient disturbances at the linear natural frequency. The transient ringing will persist for many cycles because of the low damping of the optical fiber. In this nonlinear system, a maximum amplitude 68 is displaced away from its position 70 at the linear resonant frequency, as shown in an exemplary manner in FIG. 5. Until the transient dies away, the optical fiber response will therefore consist of the drive frequency and the natural frequency. The transient and the drive frequency will interact with each other, creating the beating phenomena. At sufficiently high frame rates, the transient does not have sufficient time to die away. In this case, the amplitude of the drive signal may pass through zero, but the scan's amplitude does not, resulting in a toroidal scan rather than a spiral scan.

The phase and amplitude responses of the optical fiber are dependent upon the drive frequency and amplitude, as shown in FIG. 6. A linear amplitude relationship 74 and a linear phase relationship 76 are shown as a function of a drive amplitude $A_d$, in comparison to a nonlinear amplitude relationship 78 and a nonlinear phase relationship 80, relative to the drive amplitude. Because the drive signal is amplitude modulated, the phase of the response changes. The edges of the scan are not in phase with the center, resulting in distortion, as indicated by curved radial lines 82 relative to linear radial lines 84. This nonlinear effect also contributes to the scan's amplitude modulation decaying into and out of the triangle envelope.

Control Goals

Having identified some of the sources of distortion and their causes, controllers were developed that are able to produce reliable, distortion free scans. It is intended that a suitable optical fiber scanner control produce a scanned spot of light that perfectly tracks a reference waveform regardless of nonlinear effects and is robust to variability in the scanner that may arise due to manufacturing variations or due to the operating environment. In developing such controllers, open loop control, phase locked loops with PID amplitude control, lock-in amplifiers with PID amplitude and phase control, frequency space control with feedforward and feedback, error space control with adaptive feedforward and full state feedback, feedback linearized control, adaptive control, and robust sliding mode control were considered. The following discussion deals with differences in the various control techniques implemented in the present invention. It should be understood that the controllers shown in FIGS. 7A, 7B, 8, and 11 are only for use in controlling a drive signal applied to an optical scanner relative to a single axis. Depending on the desired pattern desired of the optical scanner, appropriate drive signals may need to be applied to both orthogonal axes, x and y, which will then require a separate controller for each axis. For the sake of simplifying the drawings, only one such controller is shown in each of these Figures.

Phase Locked Loop Controller

A survey of prior art controllers for resonant scanners finds that phase locked loop (PLL) controllers are the most common means of control. In prior art scanning systems, a resonant scanner is typically used to produce a high-frequency constant amplitude/constant phase sinusoidal scan in the horizontal direction, and a non-resonant scanner (galvo-mirror or bi-morph) typically produces a low-frequency scan in the vertical direction, thus producing a raster scan. Some systems are run open loop. Alternatively, PLLs are used to control either the frequency of the scan to produce maximum output deflection (in a scheme known as "scanner as master"), or to control the scan's phase to synchronize the scanner with an external system, e.g. an imaging system (in a scheme known as "scanner as slave"). Typically, in such controls, the amplitude of the scan is not automatically controlled, but is manually adjusted.

In the scanner as master scheme, a phase comparator in a PLL is used to compare the phase of the scanner's output to the scanner's input. Based on the phase difference, a voltage controlled oscillator (VCO) in the PLL changes the scanner's input frequency until the input phase and output phase are 90° apart, i.e., when a "linear" resonant system has its maximum amplitude output. Based on the input frequency, the image acquisition or display frequencies are appropriately adjusted to maintain synchronization with the scan. The scanner acts as a master clock, and the image system acts as a slave; hence the name "scanner as master."

In the scanner as slave scheme, a phase comparator in a PLL is used to compare the phase of the scanner output to a desired reference (which governs the image acquisition or display frequencies). Based on the phase difference, the VCO in the PLL changes the scanner's input frequency until the reference phase and output phase are 90° apart. At this point, the frequency of the scanner's output will be the same as the reference frequency. The scanner is synchronized with the external system, which is acting as a master clock, and the scanner acts as a slave—hence the name "scanner as slave."

In these systems, the amplitude of the scan is generally not controlled. The amplitude of the scan may change due to changes in the resonant properties of system with changes in environment or aging. Furthermore, the fiber's nonlinear behavior affects the scan pattern when the desired scan amplitude is changed. For instance, if the resonant optical fiber input amplitude is halved, its (horizontal) output scan amplitude may not decrease by half. If the other (vertical) scanner amplitude is halved, then the scan's horizontal/vertical aspect ratio will change, resulting in scan distortion. (The decrease in input amplitude will also be accompanied by a phase shift in the output, but the PLL controller, for the scanner as slave approach, will resynchronize the system.)

If a 1D scan is desired from a resonant optical fiber scanner, its nonlinear behavior will include cross-axes coupling. Thus, instead of producing a 1D scan line, a 2D ovular scan (whirl) is often observed. The whirl distorts the ideal raster scan. Since the prior art PLL scanner controls do not control amplitude, they cannot remove cross-axes scan.

In these prior art scanner systems with a PLL control, the scan pattern is not controlled; instead, only the phase is controlled. Although the scan from a resonant optical fiber scanner is nearly sinusoidal due to the narrow frequency range of resonant amplification, the nonlinear behavior of the optical fiber may introduce additional vibration frequencies (harmonics). These harmonics may interfere with the performance of the PLL or distort the scan.

The scanner as master scheme assumes that the maximum amplitude output occurs when the input phase and the output phase of the resonant fiber are 90° apart, which is not true for all resonant systems, especially those with damping and significant nonlinear behavior. This assumption also does not account for phase shifts (time delays) introduced by the actuator used to drive the optical fiber.

PLL controllers of the prior art are only useful for constant amplitude sinusoidal scans at a fixed phase. Amplitude is generally not controlled in such prior art scanner controls, but instead, is manually adjusted.

In the present invention, a PLL was adapted to address the problem of tracking a modulated amplitude sine wave. To control the optical fiber scanner, a standard PLL module 92 is employed to control the phase, and a PID module 94 is employed to control the amplitude, as shown for a control 90 in FIG. 7A.

To control the phase, a desired scan pattern 96 from a waveform reference 99, and the position signal output from a sensor 98 are input to a phase detector 100 of the PLL. The output of the phase detector passes through a low pass filter 104, leaving only a DC component related to the phase difference that is applied to a VCO 110. The low pass filter's output controls the frequency of the VCO. When phase locked, the frequency of the VCO should be the same as the reference, and the phase between the reference and the output should be 90°. Unlike prior art controls that include a PLL, the amplitude of the VCO is multiplied (or amplified) by the amplitude control scheme of control 90.

The amplitude control scheme includes a synchronous amplitude demodulator 102, which is used as an amplitude detector, and a PID controller. An amplitude demodulator is a standard circuit used in AM radio communications. In radio communications, the amplitude of a high frequency carrier wave is slowly varied (modulated) to encode audio information, which is then transmitted. The receiver is tuned to the high frequency carrier wave, then uses an amplitude demodulator to determine the (slowly varying) amplitude to decode the audio information.

By analogy, in an optical fiber scanner, the carrier wave corresponds to the resonant vibrations of the optical fiber. The amplitude of the fiber is determined by the amplitude demodulator as a function of a signal indicative of a sensed position of the moving portion of the optical fiber. The amplitude is then used in a standard PID feedback controller to produce a commanded input amplitude to actuator for the optical fiber. The commanded input amplitude is proportional to the error between the desired amplitude and the sensed amplitude (P), proportional to the integral (I) (sum over time) of that error, and proportional to the derivative (D) or change with respect to time of that error—hence, the name "PID controller."

Amplitude demodulator 102 takes the position measurement from a sensor and produces the modulation amplitude as an output. The amplitude of the scan from the amplitude demodulator is compared by a comparator 108 to a reference triangle modulation wave from an amplitude reference 106, and any difference (error) between the two amplitudes is driven to zero by PID module 94, which has its output coupled to a multiplier 111. The output of VCO 110 is also applied to multiplier 111 and its output is used to drive resonant optical fiber scanner 30.

FIG. 7B illustrates another control 90' that does not include PLL controller 92 for controlling phase, but instead uses another PID controller 95. A phase ($\phi$) reference 97 provides a reference phase input to PID controller 95, which is compared to a phase output signal from a dual-phase lock-in amplifier 105. A dual-phase lock-in amplifier is a standard circuit used in scientific measurements and can accurately and concurrently detect the amplitude and phase of a desired frequency from input signals even in the presence of large amounts of noise and other corrupting frequencies. PID 95 produces a phase output signal that is applied a function generator 109. Dual-phase lock-in amplifier 105 has its inputs coupled to receive signals from sensor 98 and from reference waveform source 99. An amplitude output signal from dual-phase lock-in amplifier 105 is coupled to PID 94, which also has an input connected to the reference triangle modulation wave from amplitude reference 106. The output from PID 94 is coupled to function generator 109. The function generator employs the input from PID 95 and PID 94 to produce the sine wave drive signal (Asin($\omega t=\phi$), where $\omega$ is the set frequency of waveform reference 99, A is the amplitude provided by the amplitude reference 106, and $\phi$ is the phase provided by phase reference 97) applied to actuate resonant optical fiber 30.

Either control 90 or control 90' can be used with a 2D actuator to remove whirl in a 1D scan by an optical fiber. In this case, the horizontal scan is controlled to achieve the desired amplitude and phase. The optical fiber's nonlinear behavior may cause an undesired response in the vertical direction (whirl). The amplitude controller portion of the control (PID 94 of control 90 or dual-phase lock-in amplifier 105 and PID 94 of control 90') is used with the scanner's vertical actuators and is supplied a commanded amplitude of zero. With the PID controller's command proportional to the integral of the error, the control can provide a drive input to the actuators with an appropriate phase and amplitude to cancel the whirl.

The advantage of using PLL and/or PID controller modules in controls 90 and 90' is that they do not need a dynamic model of the system and its parameters. Selection of the low pass filter characteristics of low pass filter 104 determines the dynamics of PLL 92. Selection of the gain used by control 90 determines the dynamics of the PID module. Basically, the gain is controlled by a user to achieve a desired response. Care must be taken in setting the coefficients used by the PID and choosing the low pass filter characteristics of the PLL. The optical fiber's phase and amplitude responses are interrelated. A change in one results in a disturbance and long lasting transient in the other. Because the amplitude and phase are controlled with one drive signal in control 90, the two controllers (PLL and PID) can fight each other. The responses of each in regard to the phase control and the amplitude control must be made sufficiently slow so as not to create too large a disturbance for the other to control. Also, if the PLL and PID controller modules are too aggressive in the control that they assert, the response of the system may be faster than the response of the sensor, resulting in corrupted or delayed measurements. Delays always decrease the stability of a controller.

Frequency Space Controllers and Use of a Dynamic Model

Instead of controlling the amplitude, phase, and frequency separately with PLL and PID modules, it is sometimes better to control the scan or the optical fiber to track the reference waveform directly using model based controllers. Also, by adding information about the system behavior, via a dynamic model, better performance can be obtained from a control, although at the expense of added complexity.

For a linear frequency space controller the tracking part of the controller is accomplished with feedforward by inverting the linear system dynamic model (ignoring the nonlinear behavior). Tracking is defined as the application of a calculated input to force the position of the moving portion of an optical fiber to follow a known desired reference. Tracking the optical fiber position is preferable to controlling the amplitude and the phase of wave form that drives the optical fiber. With perfect tracking, the desired amplitude, phase, frequency, and scan pattern are all simultaneously met.

Figure 8:
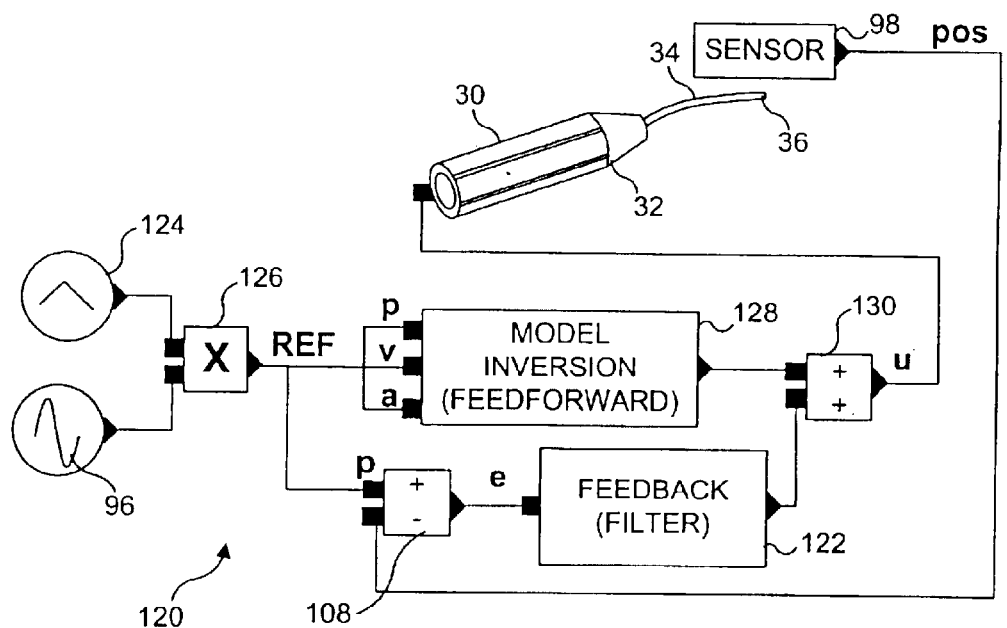
FIG. 8 is a functional block diagram of a frequency space tracking controller with feed forward for controlling an optical fiber scanner.

A controller 120, shown in FIG. 8, computes an input to resonant optical fiber scanner 30 required to achieve a desired output, based upon a system (plant) dynamic model. The dynamic model used in this controller describes how the fiber output is related to the frequency and amplitude of the actuator input and to system parameters such as system damping, actuator strength, and optical fiber natural frequency. Using this model, it is possible to calculate an appropriate input to achieve a desired output (e.g., a constant amplitude, a constant phase sinusoid, or an amplitude modulated sinusoid). This use of a model is called "plant-inversion," feedforward, or back-propagation, and does not require feedback of the optical fiber position. A filtered feedback of the optical fiber position (of the tip or other moving portion of the optical fiber that affects the tip position) stabilizes the system and increases the rejection rate of disturbances in the system.

An error feedback module 122 in control 120 provides stabilization of the overall system and error dynamics. With a proper choice of a filter for the feedback signal, the error will result in asymptotic tracking for a linear system. To perform feedforward control, control 120 needs a desired position, velocity, and acceleration, which are based upon a reference signal set produced by combining desired signal 96 and a triangle waveform amplitude 124 with a multiplier 126 which provides position, velocity, and acceleration inputs to a model inversion (feedforward) module 128. The feedforward output signal is added to the feedback signal by an adder 130, producing the output signal used to drive resonant optical fiber scanner 30. To perform the error feedback, control 120 only needs the position of the distal tip of the optical fiber, which is provided from sensor 98. The position of the optical fiber is compared to the reference position by comparator 108, producing an error signal e. The feedback module processes the error signal, producing the signal supplied to adder 130.

Figure 9:
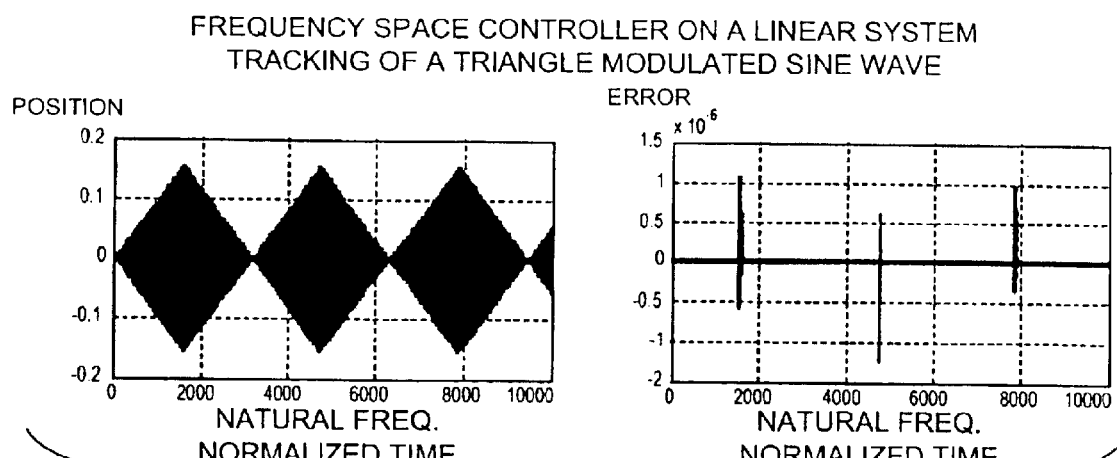
FIG. 9 illustrates graphs of position and tracking error versus natural frequency normalized time for a linear control model.

It is a commonly accepted practice in the art to design a control using a linear model of a system, and then to test it on a nonlinear system. When performing simulations on a linear system (plant) for a spiral scan, control 120 is able to asymptotically track a triangle modulated sine wave in both the horizontal and vertical axes, except at discontinuities. At the discontinuities, there is a jump in the error, then the response exponentially decays to zero in the steady state, as shown in FIG. 9.

Figure 10:
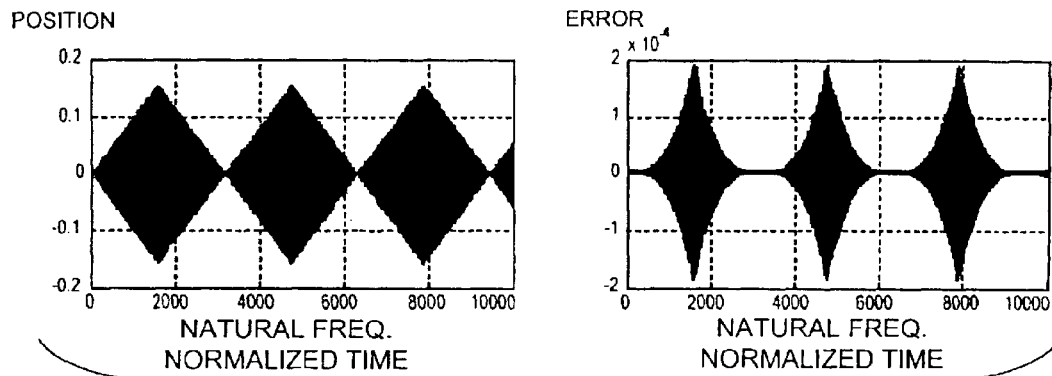
FIG. 10 illustrates graphs of position and tracking error versus natural frequency normalized time for a non-linear control model.

For a nonlinear system, the steady state error is an exponentially ramped sinusoid, as indicated in FIG. 10. At the discontinuities, the error doesn't appear to jump in magnitude. The error can be reduced by increasing the amount of feedback, but doing so tends to destabilize the system. The tracking controller is also sensitive to model inaccuracies, including model parameter variations and nonlinear effects, because the model is used to calculate the necessary input for the desired output.

Robust Error-Space Controller

Figure 11:
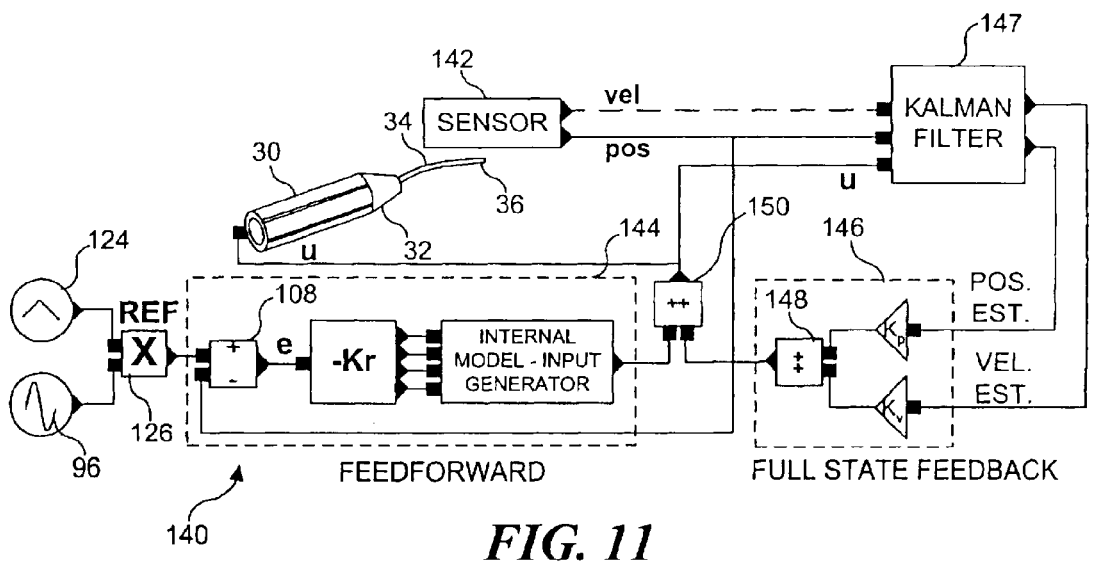
FIG. 11 is a functional block diagram of an error-space controller with feed forward.
Figure 12:
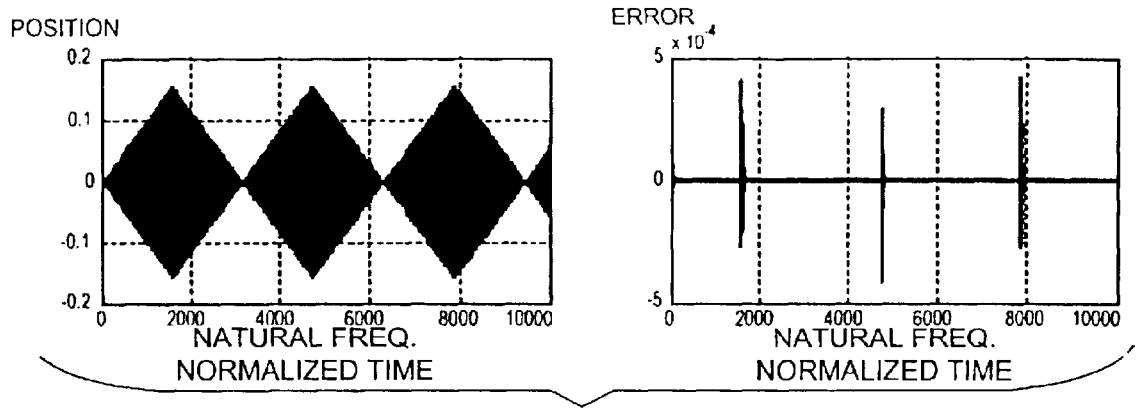
FIG. 12 illustrates graphs of position and tracking error versus natural frequency normalized time for a modern error-space controller with feed forward on a linear model.

Another linear controller used for asymptotic tracking and robust to parameter variations, is an error-space controller 140, shown in FIG. 11. This controller employs equations for the reference waveform and equations for the scanner's dynamics, and derives the system's error dynamics. The problem of tracking is reformulated into driving the error to zero. A sensor 142 provides signals indicative of the position (and optionally velocity) of the distal tip of the resonant optical fiber. If a velocity measurement is not available, an estimate can be made from a low pass filtered derivative of the position measurement, or by a Kalman filter provided with the position measurement and the actuator input. The Kalman filter provides a position estimate and a velocity estimate from noisy position (and optionally velocity) measurements. The sensor position signal or the Kalman filter's position estimate is also input to comparator 108 and compared to the reference position, producing the error signal, e. The error-space controller uses the position error in a feedforward module 144 to adjust the input model for feed forward tracking and robustness for modeling inaccuracies. It also uses a full state feedback module 146, which receives the position and velocity estimate signals from the Kalman filter to stabilize the system and remove disturbances. For full stale feedback, the estimated optical fiber tip position and velocity must be known, and their values are employed to produce a combined feedback signal provided at an output of an adder 148. The output of adder 148 is combined with the output of the feedforward module by an adder 150, producing the input signal used to drive the resonant optical fiber scanner. Simulations show that such a control asymptotically tracks the ramped sinusoid for a linear system, but that error jumps at the peak discontinuity and exponentially decays to zero afterwards, as shown in FIG. 12.

Figure 13:
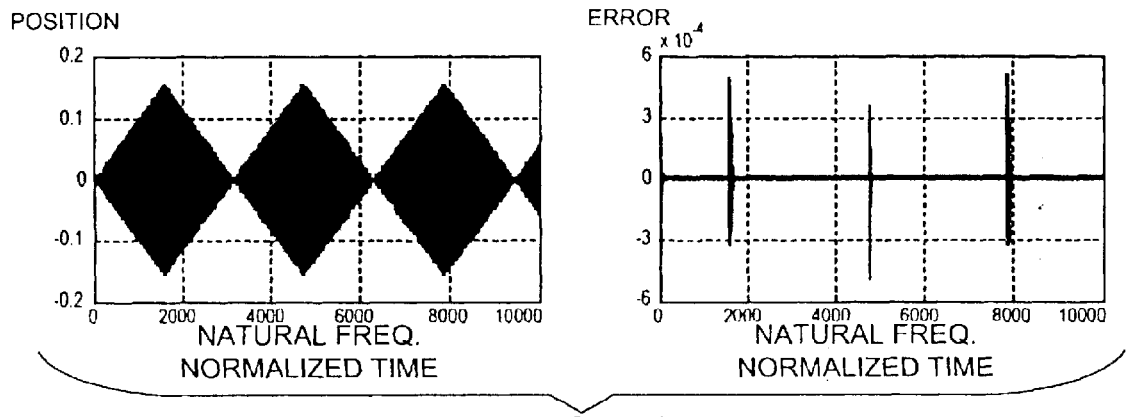
FIG. 13 illustrates graphs of position and tracking error versus natural frequency normalized time for a modern error-space controller with feed forward on a non-linear model.

For the nonlinear system, the error is still a ramped sinusoid, but much smaller than the frequency space controller results on a nonlinear system. At the peak discontinuity, the error jumps, but dies away exponentially, returning to the low level ramped sinusoid as shown in FIG. 13. Most of the steady state error is due to phase error, as evidenced by a close examination of the plots shown in these Figures, from which it will be evident that the reference and error plots are similar.

Nonlinear Control

In the above examples, the use of linear controls resulted in steady-state errors when applied to nonlinear systems or plants. As mentioned above, it is preferable if the control is able to cause a scan to asymptotically track a reference. It is important to note that each of the linear controls discussed above is able to asymptotically track the linear plant, except at discontinuities, and after experiencing a discontinuity, the tracking error asymptotically decays to zero.

An important class of nonlinear controllers employs feedback linearization. In feedback linearization, an additional control function is included to cancel out nonlinearities. The desired effect is to render the system dynamics linear. The original equations for the system are:

$$\ddot{x}+b\dot{x}+x+\epsilon x(x^2+y^2)+\epsilon x(\dot{x}^2+\dot{y}^2)=Cu_x$$

$$\ddot{y}+b\dot{y}+y+\epsilon y(x^2+y^2)+y(\dot{x}^2+\dot{y}^2)=C_y$$

Adding a new control function to cancel nonlinearity results in:

$$\ddot{x} + b\dot{x} + x + \varepsilon x(x^2 + y^2) + \varepsilon_2 x(\dot{x}^2 + \dot{y}^2) = C\left[u_x + \frac{\varepsilon x(x^2+y^2) + \varepsilon_2 x(\dot{x}^2+\dot{y}^2)}{C}\right]$$

$$\ddot{y} + b\dot{y} + y + \varepsilon y(x^2 + y^2) + \varepsilon_2 y(\dot{x}^2 + \dot{y}^2) = C\left[u_y + \frac{\varepsilon y(x^2+y^2) + \varepsilon_2 y(\dot{x}^2+\dot{y}^2)}{C}\right]$$

The system then acts like a linear system:

$$\ddot{x}+b\dot{x}+x=C\bar{u}_x$$

$$\ddot{y}+b\dot{x}+y=C\bar{u}_y,$$

$$\bar{u}_x = u_x + \frac{\varepsilon x(x^2+y^2) + \varepsilon_2 x(\dot{x}^2+\dot{y}^2)}{C}$$

$$\bar{u}_y = u_y + \frac{\varepsilon y(x^2+y^2) + \varepsilon_2 y(\dot{x}^2+\dot{y}^2)}{C}$$

Therefore, linear controllers can be applied to nonlinear systems and can achieve results predicted by the linear model used by the linear controller—asymptotic tracking.

Figure 14:
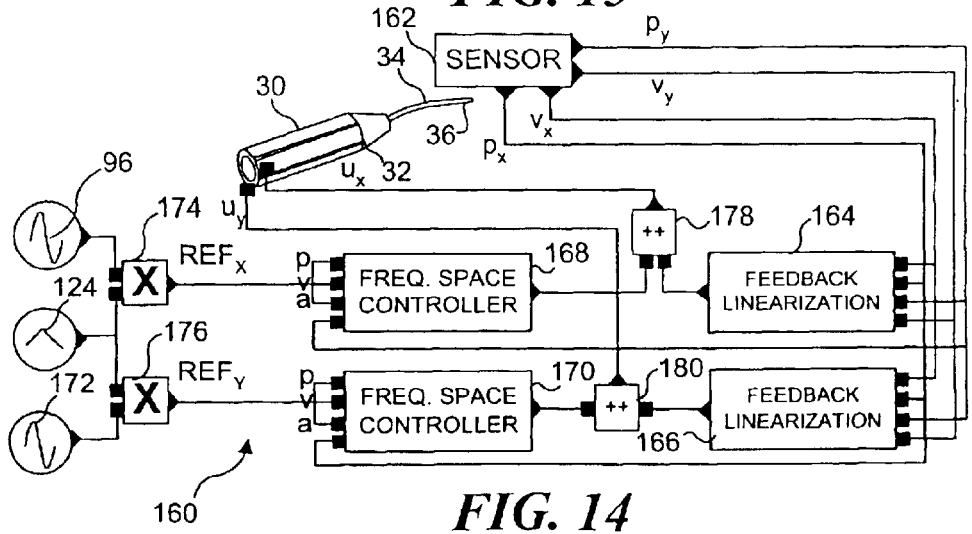
FIG. 14 is a functional block diagram of a frequency space tracking controller with feedback linearization.

The functional components for tracking control with feedback linearization and modern error-space control with feedback linearization are respectively shown in regard to a control 160 and a control 190, which are respectively shown in FIGS. 14 and 15, discussed below. The responses of control 160 are not shown, but are identical to the linear model results shown in the Figures for the respective linear controller sections.

Tracking Controller with Feedback Linearization

In control 160, frequency space tracking controls 168 and 170 for the x and y axes, respectively, use feedback linearization modules 164 and 166 to cancel out the nonlinear effects with respect to each axis. Each of frequency space tracking controls 168 and 170 includes the controller shown in FIG. 8, i.e., includes the model inversion (feedforward) module, and the feedback module, as well as the other components of controller 120 and is used for controlling the drive signal for one of two orthogonal axes, x and y. As shown in FIG. 14, desired periodic waveform patterns 96 and 172 (for the x and y axes, respectively) are combined with triangle waveform amplitude 124 in multipliers 174 and 176 to provide x and y axes reference signals that are input to tracking controls 168 and 170, respectively. Feedback of the x and y positions of the distal tip of the optical fiber is supplied from a position sensor 162 to controls 168 and 170 and to feedback linearization modules 164 and 166. The output signals from the tracking controls and from the feedback linearization modules are added by adders 178 and 180 for the x and y axes, respectively, producing output signals that drive the resonant optical fiber scanner relative to both the x and y axes.

Thus, feedforward is used to compute the input to give the desired output, the feedback signal is employed to stabilize the system and remove disturbances, and feedback linearization is added to remove nonlinear behavior. Control 160 asymptotically tracks the triangle amplitude modulated sine wave, except at discontinuities. After a discontinuity, there is a jump in error that exponentially decays to zero. Tracking controls 168 and 170 require the reference position, velocity, and acceleration (supplied from multipliers 174 and 176), and the output from position sensor 162. The tracking controls are sensitive to model inaccuracies, which may lead to steady state errors.

Error-Space Controller with Feedback Linearization

Figure 15:
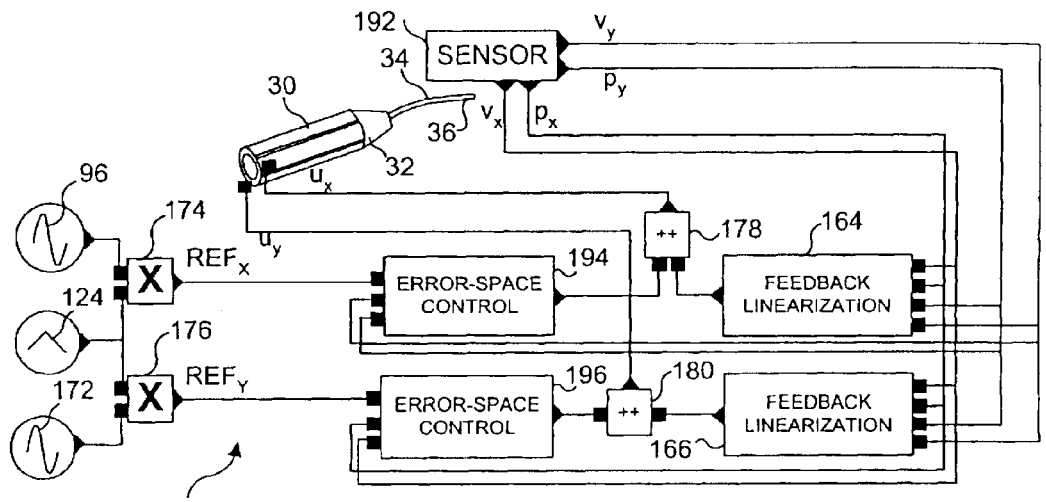
FIG. 15 is a functional block diagram of a modern error-space controller with feedback linearization.

A control 190 in FIG. 15 uses a number of the same components as control 160, but includes error-space controls 194 and 196. Each error-space control 194 and 196 includes the components of controller 140 (FIG. 11) and is used to control the drive signal applied to a different one of the x and y axes of the optical scanner. A position and velocity sensor 192 provides position and velocity for both the x and y axes (or velocity can be computed as the first derivative of the position with respect to time for each axis or estimated from a Kalman filter). Feedback linearization modules 164 and 166 are employed in this controller to cancel out nonlinear effects, full-state feedback is employed to stabilize the system and remove disturbances, and adaptive feedforward uses an input model for tracking and robustness. Control 190 is able to asymptotically track the triangle amplitude modulated sine wave except where there is a discontinuity. After a discontinuity, there is a jump in error, which exponentially decays to zero. The error-space control requires the reference position (supplied from multipliers 174 and 176), and the tip position and the velocity of the tip, and is insensitive to inaccuracies in the parameters of the linear model.

Sensors for Feedback Control

Typically, the implementation of closed-loop feedback control requires the measurement or determination of fiber dynamics. Sensors are used to determine frequency, position, and/or functional equivalents of the optical fiber motion in order to determine the optical fiber tip position (also, velocity of the distal tip) over time. For example, sensors on the surface of the optical fiber scanner can be used to measure the bending of the optical fiber along the axis on which the sensor is placed. In FIGS. 16A and 16B, sensors 208 and 210 are shown mounted on a base 202 of a tapered optical fiber 200, for both linear optical fiber scanning and 2D optical fiber scanning, respectively. In FIG. 16B, two sensors 212 (only one shown) are mounted on opposite sides of the optical fiber, at positions generally orthogonal to those of sensors 208 and 210. A cantilevered tapered portion 204 of the optical fiber has a distal end 206 that is resonantly driven as shown in the Figures. The sensors can measure optical fiber bending with one of several mechanisms, such as electromechanical and optical. An electromechanical sensor made from a piezoelectric film or micro-strain gauge can measure compressive and tensile forces as the sensor bends with the optical fiber. An optical sensor made from a photodiode material can measure increases in light leakage as the optical fiber bending increases transverse to the longitudinal axis of the optical fiber (decreasing its radius of curvature). In FIG. 16A, the distal tip swings at a near resonant amplitude from an extreme displacement in one direction, as shown by the solid lines, to an extreme displacement in an opposite direction as shown by the dash lines. The arc of the distal tip of the waveguide is proportional to the optical FOV for the linear scan. Sensors 208 and 210, which are used for monitoring the movement of the distal tip, are shown overlying piezoelectric bimorph actuators 209 that drive the optical fiber to move in response to an applied drive signal, but it will be appreciated that the sensors are mounted separately from the actuators, and can be mounted at a variety of locations on the optical fiber, adjacent to the distal end. The sensors are coupled to an external control (not shown), such as those discussed above.

Dual sensors 208/210, and dual sensors 212, which are provided along each of two orthogonal axes of bending, as shown in FIG. 16B, increase the signal-to-noise ratio of the measurement and are preferred. Alternative methods can employ sensing apparatus and techniques conventionally used for determining the relative position of scanned probes, such as near-field scanning optical microscopy, shear-force microscopy, and atomic force microscopy.

A new method has been developed for remote sensing of the displacement of the distal tip of an optical fiber or waveguide, employing only optical techniques. This method takes advantage of the strain birefringence inherent in most optical fibers. By doing so, the need for integrated displacement-sensing hardware is eliminated, which keeps the size of the resonant scanning optical fiber relatively compact. In applications where the sensor or optical fiber scanner needs to be disposable, such as micro-endoscopes employing optical fiber scanning technology, the overall cost and complexity of the design is also considerably reduced.

In this approach to sensing the displacement of the distal tip, advantage is taken of the inherent strain birefringence of an optical fiber by sending polarized light down the optical fiber. This polarized light may be conveyed at a wavelength that is different than that of the light used for other functions of the device. As the optical fiber is displaced, the polarized light is increasingly repolarized and also, depolarized to some degree. The repolarization of the light is relied upon as a primary measure of the displacement of the optical fiber, but depolarization, bending losses (independent of polarization), and changes in degree of coherence can alternatively be used. This technique of measuring repolarized light is advantageous over bending-loss measurement schemes, because it yields a signal only when the optical fiber is stressed, thus improving the signal-to-noise ratio of the measurement. Bending-loss only schemes produce a small reduction in a large signal and suffer from poor signal-to-noise ratio.

The simplest remote-sensing hardware configuration includes a single photosensor and a polarizing filter. The axis of the polarizing filter is positioned at 90° to the initial polarization vector of the light in the optical fiber (before fiber bending), so that only repolarized light is transmitted through the polarizing filter to the photosensor. A more complex configuration with two photosensors, yields a normalized measurement of light intensity and enables depolarization measurements to be made. Since this method is also capable of measurement of polarization vector rotation through a 90° range, repolarization can be more directly measured than in the single photosensor configuration, where repolarization is inferred from transmitted intensity.

Figure 17:
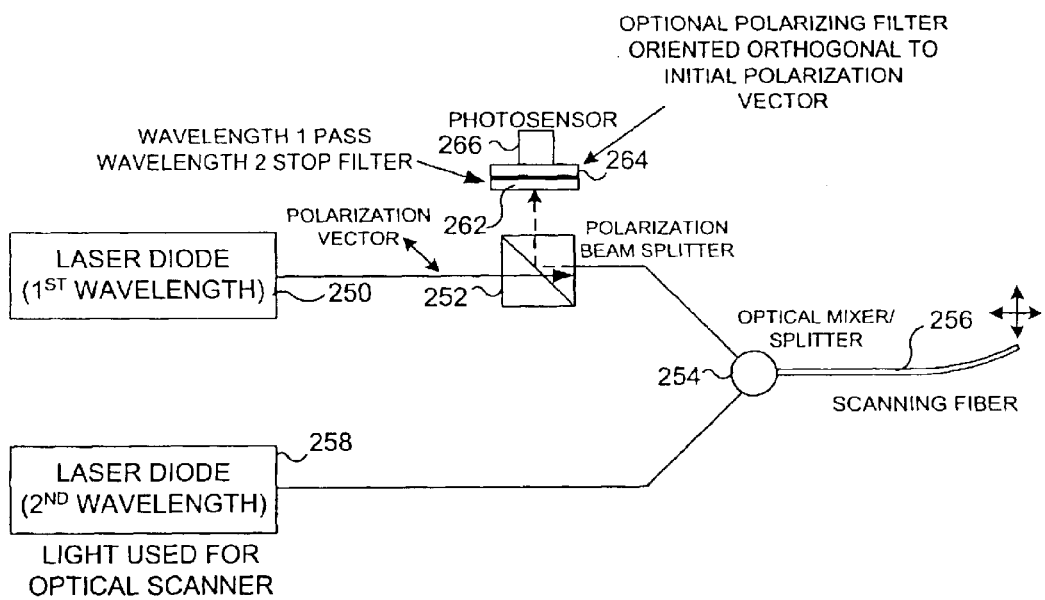
FIG. 17 is a functional block diagram of a system for remote sensing of the position of the distal tip of an optical fiber scanner.

If an increase in the intensity of back-reflected light from the distal tip is needed for accurate sensing, a thin metal (e.g., chrome, then aluminum) layer may be deposited at the distal tip of the optical fiber or waveguide as necessary to create a mirror-type beam splitter of desired transmission/reflection ratio. FIG. 17 shows one exemplary configuration of a displacement sensor in which displacement can be measured using polarized light. When an optical fiber is deflected or bends, the stress acting on the optical fiber changes the orientation or repolarizes the polarization vector of polarized light that is traveling through the optical fiber.

The sensor in FIG. 17 detects this repolarization to determine the position of an optical fiber as it moves and bends. As shown in this Figure, a laser diode 250 (or other suitable light source) produces polarized light having a first wavelength, and a laser diode 258 produces light having a second wavelength that is different than the first and is used for scanning by an optical scanner 256. The two light beams are combined by an optical mixer/splitter 254 and travel into the moving portion of optical scanner 256. Repolarized light caused by the bending of this moving portion of scanning optical fiber 256 travels back through optical mixer/splitter 254 and is split, traveling back into polarization beam splitter 252. The repolarized light redirected by polarization beam splitter 252 is directed to a first wavelength pass filter and a second wavelength stop filter 262, and through an optional polarization filter 264. Polarization filter 264 has its polarization axis oriented to pass light having a polarization vector that is orthogonal to the original polarization vector of the light from laser diode 250. Thus, a photosensor 266 is disposed to monitor the intensity of the light passing through polarizing filter 264, which is indicative of the deflection of the optical scanning fiber. This sensor can be simplified by using light of the same wavelength for both scanning and for detecting the deflection of the optical scanner.

A major application for this remote-sensing system is for use with a control of an optical fiber scanner, such as the controls discussed above. This sensing method has a high bandwidth and can be implemented in real-time (i.e., with extremely small latency times <10 microseconds), which allows mapping of the optical fiber tip position during scanning. A remapping step can be used to remap the intensity data for image display or acquisition to minimize distortions. The above-described scheme only measures displacement and not absolute position of the optical fiber.

Figure 18:
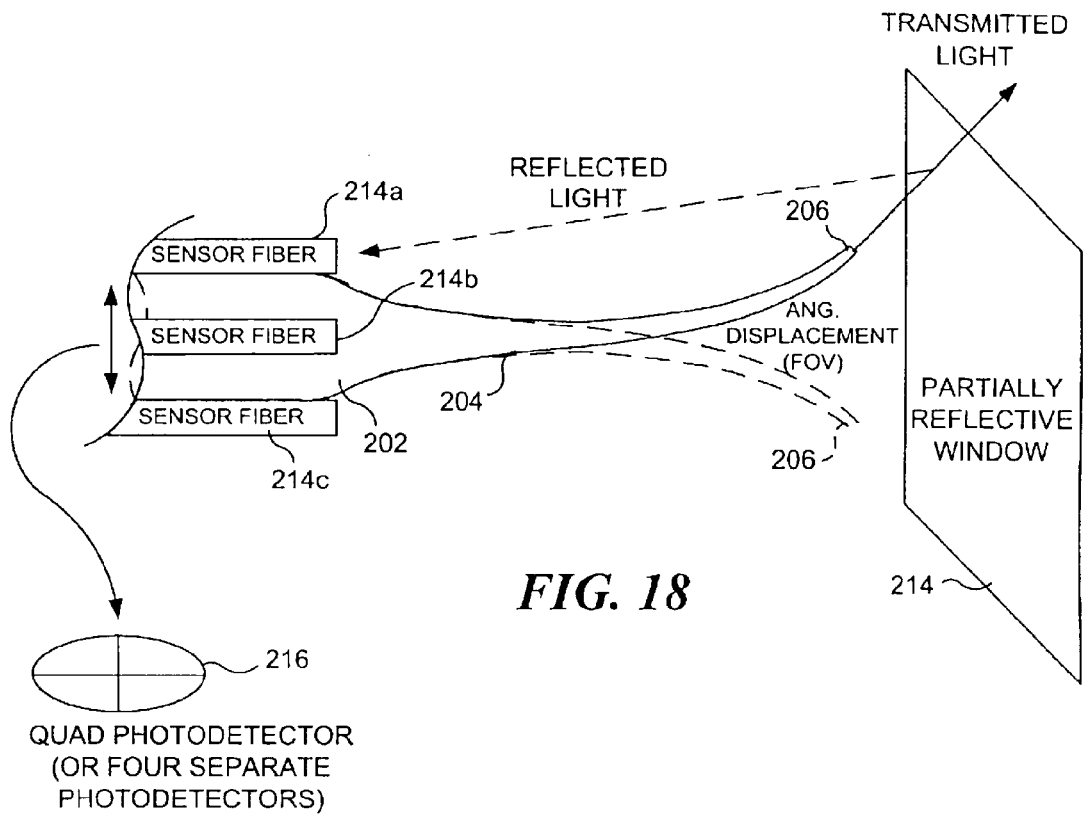
FIG. 18 is a schematic diagram illustrating a plurality of multimode optical fibers that are used to convey light to a proximal quad light sensor for determining a position of the distal tip of the resonant optical fiber.

Yet another sensor scheme for monitoring the position of distal tip 206 of a resonant scanning optical fiber is illustrated in FIG. 18. In this scheme, four sensor optical fibers (multimode) are arrayed at orthogonally opposed positions around base 202 of the optical fiber whose moving distal tip is being monitored. Only sensor optical fibers 214*a*, 214*b*, and 214*c* are visible in FIG. 18, since the fourth sensor optical fiber is disposed opposite sensor optical fiber 214*b* and is behind the base and not visible in the Figure. A partially reflective window 214 is provided to reflect light emitted from distal tip 206 back toward the sensor optical fibers. The light reflected back from partially reflective window 214 passes through the sensor optical fibers and is conveyed proximally, to illuminate a quad photodetector 216 (or other 2D detector or group of detectors). The quad photodetector responds to the light traveling through sensor optical fibers, producing a signal that is indicative of the position of distal tip 206. This signal can be processed to determine a first derivative of position with respect to time, to determine a velocity for the distal tip.

Optical Fiber with Mass at Distal Tip

Figure 19:
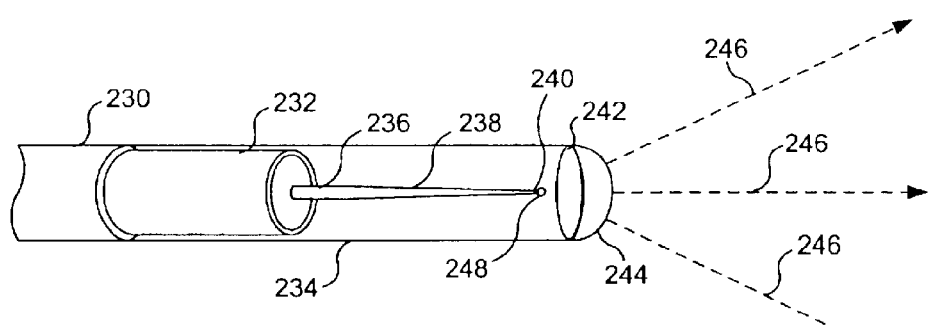
FIG. 19 is a schematic diagram of a tapered optical fiber scanner that includes a micro-lens (i.e., an additional mass) at a distal end of the tapered optical fiber.

In FIG. 19, a tapered portion 238 of an optical fiber 236 is attached to the distal end of a piezoelectric actuator 232, close to the proximal end of the tapered portion. The exact point of attachment, mechanical properties of the waveguide, and taper geometry determine the resonance frequencies of the optical fiber. The actuation, amplitude, and frequency of the piezoelectric actuator determine the amplitudes of optical fiber displacement and deflection of a distal tip 240, its frequency, and the optical scanning pattern it describes. Typically, an optical fiber cantilever is extended from about 1 mm to about 4 mm out from its point of attachment at the end of the piezoelectric bimorph to achieve high FOV scanning frequencies, i.e., greater than 18 kHz. The opposite end of the piezoelectric actuator is held fixed (e.g., epoxied to the end of a steel tube 230). Thus, both micro-fabricated optical fiber 236 and the actuator are cantilevered in a fixed-free boundary condition. A protective tube 234 surrounds the optical fiber and the actuator. At the fixed end, piezoelectric electrodes (not shown) on the actuator are connected by fine wires (also not shown) to one of the controls discussed above, which drives the optical fiber with a controlled sinusoidal waveform of variable voltage (amplitude) at a desired frequency (e.g., adjustable from about 1 kHz to about 100 kHz).

Separate imaging and/or scan lenses 242 and 244 can be disposed adjacent to the tip of the micro-fabricated fiber scanner to generate focused linear and 2D scan patterns onto a screen. Furthermore, a micro-lens 248 is fabricated onto distal tip 240 of optical fiber 236, as shown in FIG. 19, to focus light 246 emitted by the scanning optical fiber. The micro-lens represents a small additional mass that is readily accounted for in any of the controls discussed above.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A controller for an optical scanner that is driven to move in a desired pattern, comprising:
   (a) a first reference phase signal source that produces a reference phase signal;
   (b) a first phase control that is adapted to couple to a sensor to receive a position signal indicative of a position of a moving portion of the optical scanner and to the first reference phase signal source to receive the reference phase signal, said first phase control using the reference phase signal and the position signal to produce a phase signal output;
   (c) a first amplitude reference source that produces an amplitude reference signal; and
   (d) a first amplitude control that is adapted to couple to a sensor to receive the position signal and to the first amplitude reference signal source to receive the amplitude reference signal, said first amplitude control producing an amplitude signal output in response to the position signal and the amplitude reference signal, wherein the phase signal output and the amplitude signal output are combined to control a drive signal used to drive the optical scanner to move in the desired pattern.

2. The controller of claim 1, wherein the first phase control comprises a phase locked loop, said phase locked loop varying the phase signal output so as to achieve a predefined relationship between the reference phase signal and a phase of the optical scanner.

3. The controller of claim 1, wherein the first amplitude control comprises:
   (a) an amplitude demodulator that receives the position signal and determines an amplitude of the optical scanner, and
   (b) a proportional-integral-derivative feedback controller coupled to the amplitude demodulator and producing the amplitude signal output so as to minimize an error in the amplitude of the optical scanner relative to the amplitude reference signal.

4. The controller of claim 1, wherein the first phase control comprises:
   (a) a dual-phase lock-in amplifier that is coupled to the sensor and to receive a reference waveform, said dual-phase lock-in amplifier having a phase output and an amplitude output; and
   (b) a first proportional-integral-derivative feedback controller coupled to the dual-phase lock-in amplifier to receive the phase output, said first proportional-integral-derivative feedback controller producing the phase signal output.

5. The controller of claim 4, wherein the first amplitude control comprises:
   (a) the dual-phase lock-in amplifier; and
   (b) a second proportional-integral derivative feedback controller coupled to the dual-phase lock-in amplifier to receive the amplitude output, said second proportional-integral-derivative feedback controller producing the amplitude signal output.

6. The controller of claim 5, further comprising a function generator that is coupled to the first and the second proportional-integral-derivative feedback controllers to receive the phase signal output and the amplitude signal output, said function generator producing the drive signal.

7. The controller of claim 1, wherein the desired pattern comprises one of a raster scan, a sinusoidal scan, a toroidal scan, a spiral scan, and a propeller scan.

8. The controller of claim 1, wherein the reference phase signal is a periodically varying waveform.

9. The controller of claim 1, wherein the reference amplitude signal has a time-varying amplitude.

10. The controller of claim 1, wherein the reference amplitude signal has a fixed amplitude.

11. The controller of claim 1, further comprising a sensor that produces the position signal indicative of the position of the moving portion of the optical scanner.

12. The controller of claim 11, wherein the sensor comprises a photosensor that is responsive to stress-induced changes in a polarization vector of polarized light traveling through the optical scanner, said changes being caused by bending of the portion of the optical scanner that is in motion, said first photosensor producing a sensor signal indicative of the position of the optical scanner relative to a first axis.

13. The controller of claim 11, wherein the sensor comprises:
   (a) a plurality of sensor optical fibers disposed in an array about the optical scanner, said plurality of sensor optical fibers extending proximally of the portion of the optical scanner that is in motion;
   (b) a partially reflective surface disposed to reflect a portion of light emitted from the optical scanner back toward the plurality of sensor optical fibers, said portion of the light being conveyed through the plurality of sensor optical fibers; and (c) a plurality of photodetectors disposed to receive the light conveyed through the plurality of sensor optical fibers, each of the plurality of photodetectors receiving light conveyed through a different one of the plurality of sensor optical fibers and producing an output from which the signal indicative of the position of the optical scanner is determined.

14. The controller of claim 1, further comprising a second reference phase signal source that produces a second reference phase signal, said first reference phase signal source and said second reference phase signal source being used to drive the optical scanner in a desired two-dimensional pattern.

15. The controller of claim 1, further comprising a second phase control that is adapted to couple to a sensor to receive a position signal indicative of a position of the moving portion of the optical scanner.

16. The controller of claim 1, further comprising a second amplitude reference source that produces a second amplitude reference signal, wherein said first amplitude reference source and said second amplitude reference signal source are used to drive the optical scanner in a desired two-dimensional pattern.

17. The controller of claim 1, further comprising a second amplitude control.

18. A controller for an optical scanner that is driven to move in a desired pattern, comprising:

(a) a reference signal source that produces at least one reference signal;

(b) a feedforward controller that operates in accord with a model of the optical scanner and is coupled to the reference signal source to receive said at least one reference signal, said feedforward controller employing the model and said at least one reference signal to determine a feedforward signal required to produce movement of the optical scanner in the desired pattern; and (c) a feedback controller that is adapted to couple to a sensor to receive a sensor signal indicative of movement by the optical scanner, said feedback controller using the sensor signal to determine a feedback signal used to stabilize the controller and to reject disturbances of the optical scanner, wherein said feedforward signal and said feedback signal are combined to control a drive signal used to drive the optical scanner to move in the desired pattern.

19. The controller of claim 18, wherein the feedback controller includes a filter for stabilizing the controller, said feedback controller being coupled to the reference signal source to receive the reference signal for use in determining the feedback signal.

20. The controller of claim 19, wherein the reference signal source produces a reference position, a reference velocity, and a reference acceleration that are input to the feedforward controller.

21. The controller of claim 18, wherein the feedback controller uses a reference position to determine the feedback signal.

22. The controller of claim 18, wherein the model is a linear dynamic model.

23. The controller of claim 18, wherein the model is a nonlinear dynamic model that has been linearized.

24. The controller of claim 18, wherein the feedforward controller is adapted to couple to a sensor to receive a sensor signal indicative of movement by the optical scanner.

25. The controller of claim 18, wherein the model used by the feedforward controller combines a model of a desired waveform for driving the optical scanner and a model of dynamic parameters of the optical scanner.

26. The controller of claim 18, wherein the reference signal is indicative of a reference position and wherein the feedforward controller determines a difference between the reference position and a position of a portion of the optical scanner that is moving within the model to derive the feedforward signal in error space.

27. The controller of claim 18, further comprising a Kalman filter that receives the drive signal and is adapted to couple to a sensor to receive a sensor signal indicative of movement by the optical scanner, said Kalman filter having an output for a position of the optical scanner and an output for a velocity of the optical scanner that are coupled to the feedback controller for use in producing the feedback signal.

28. The controller of claim 18, wherein the reference signal source includes a reference for a variable amplitude and a reference for a periodically varying waveform.

29. The controller of claim 18, wherein the reference signal source includes:

(a) a reference for a variable amplitude;

(b) a reference for a periodically varying waveform for each of two orthogonal axes; and (c) multipliers for multiplying a periodically varying waveform for each of the two orthogonal axes by a variable amplitude produced by the reference for the variable amplitude, to produce a first axis reference signal and a second axis reference signal.

30. The controller of claim 29, wherein the drive signal for each of two orthogonal axes is controlled, and wherein the first axis reference signal provides a reference position, a reference velocity, and a reference acceleration for the one of the two orthogonal axes, and the second axis reference signal provides a reference position, a reference velocity, and a reference acceleration for the other of the two orthogonal axes.

31. The controller of claim 30, further comprising a feedback linearization control for each of the two orthogonal axes.

32. The controller of claim 29, wherein error-space control of the drive signal is provided for each of two orthogonal axes.

33. The controller of claim 32, further comprising a feedback linearization control for each of the two orthogonal axes.

34. The controller of claim 18, further comprising a sensor that produces the position signal indicative of the position of a moving portion of the optical scanner.

35. The controller of claim 34, wherein the sensor comprises a photosensor that is responsive to stress-induced changes in a polarization vector of polarized light traveling through the optical scanner, said changes being caused by bending of the portion of the optical scanner that is in motion, said photosensor producing a sensor signal indicative of the position of the optical scanner relative to an axis.

36. The controller of claim 34, wherein the sensor comprises:

(a) a plurality of sensor optical fibers disposed in an array about the optical scanner, said plurality of sensor optical fibers extending proximally of the portion of the optical scanner that is in motion;

(b) a partially reflective surface disposed to reflect a portion of light emitted from the optical scanner back toward the plurality of sensor optical fibers, said portion of the light being conveyed through the plurality of sensor optical fibers; and (c) a plurality of photodetectors disposed to receive the light conveyed through the plurality of sensor optical fibers, each of the plurality of photodetectors receiving light conveyed through a different one of the plurality of sensor optical fibers and producing an output from which the signal indicative of the position of the optical scanner is determined.

37. A method for controlling an amplitude and a phase used to drive an optical scanner to move in a desired pattern, comprising the steps of:

(a) providing at least one reference phase signal;

(b) producing a phase signal output in response to said at least one reference phase signal and in response to a position signal that is indicative of a position of a moving portion of the optical scanner in regard to at least one of a pair of orthogonal axes;

(c) providing at least one amplitude reference signal;

(d) producing an amplitude signal output in regard to at least one of the pair of orthogonal axes in response to said at least one amplitude reference signal and in response to the position signal; and (e) combining the phase signal output and the amplitude signal output for each of least one of the pair of orthogonal axes, to produce a drive signal for use in driving the optical scanner to move in the desired pattern.

38. The method of claim 37, wherein the step of producing the phase signal output is done with a phase locked loop that achieves a predefined relationship between the reference phase signal and the phase of the optical scanner for at least one of the pair of orthogonal axes.

39. The method of claim 38, where the step of producing the amplitude output signal is done with an amplitude demodulator and a proportional-integral-derivative feedback controller that controls the amplitude signal output so as to minimize an error in the amplitude of the optical scanner relative to the amplitude reference signal for at least one of the pair of orthogonal axes.

40. The method of claim 37, wherein steps (b) and (d) are carried out using a dual-phase lock-in amplifier and two proportional-integral-derivative feedback controllers for each axis.

41. The method of claim 37, further comprising the step of producing the drive signal for driving the optical scanner in regard to each axis of the pair of orthogonal axes, said drive signal producing a desired movement of the optical scanner about only one of the axes, the drive signal including a component acting on the other of the axes so as to cancel out a whirl error.

42. A method for controlling an amplitude and a phase used to drive an optical scanner to move in a desired pattern, comprising the steps of:

(a) providing a reference signal for at least one of a pair of orthogonal axes;

(b) using a model of the optical scanner to determine a feedforward signal required to produce movement of the optical scanner in the desired pattern, in response to the reference signal, for at least one of the pair of orthogonal axes;

(c) producing a feedback signal for use in stabilizing control of the optical scanner and for rejecting disturbances of the optical scanner; and (d) combining the feedforward signal and the feedback signal to produce a drive signal for use in driving the optical scanner to move in the desired pattern relative to at least one of the orthogonal axes.

43. The method of claim 42, further comprising the steps of:

(a) approximating a continuous control input to the model so as to drive a tracking error in the motion of the optical scanner toward a zero value for at least one axis; and (b) providing a discontinuous control input that is determined as a function of an upper bound on an uncertainty in the model, so that the optical scanner is controlled even though the model is incomplete.

44. The method of claim 42, further comprising the steps of:

(a) applying feedback linearization by using the model to estimate a nonlinear behavior of the optical scanner for at least one axis; and (b) providing an addition to the drive signal based upon the estimate, to cancel a nonlinear behavior for at least one axis.

45. The method of claim 44, further comprising the step of adjusting model parameters based upon a sensed position of the optical scanner and the drive signal, for at least one axis.

46. The method of claim 45, wherein the model parameters are adjusted using at least one of feedback linearization and model inversion.

47. The method of claim 45, further comprising the steps of:

(a) determining a frequency of maximum amplitude of movement by the optical scanner as a function of the model parameters;

(b) changing a frequency of the reference, in regard to position of the optical scanner; and (c) using the frequency that was determined for the drive signal.

48. The method of claim 42, further comprising the step of producing the drive signal for driving the optical scanner in regard to each axis of the pair of orthogonal axes, said drive signal producing a desired movement of the optical scanner about only one of the axes, the drive signal including a component acting on the other of the orthogonal axes so as to cancel out a whirl error.

49. A method for controlling an optical scanner to produce a spiral scanning pattern, comprising the steps of:

(a) providing sinusoidally varying reference signals for each of two orthogonal axes of motion for the optical scanner, one of said sinusoidally varying reference signals being substantially 90° out of phase with the other;

(b) providing a periodically varying amplitude signal for each of the two orthogonal axes, said periodically amplitude signal having a substantially triangular waveform with a frequency substantially less than that of the sinusoidally varying reference signals;

(c) combining the sinusoidally varying reference signal for one axis with the periodically varying amplitude signal to produce a drive signal for said one axis; and (d) combining the sinusoidally varying reference signal for the other axis with the periodically varying amplitude signal to produce a drive signal for the other axis.

50. A method for controlling an optical scanner to produce a propeller scanning pattern, comprising the steps of:

(a) providing a sinusoidally varying reference signal for each of two orthogonal axes of motion for the optical scanner;

(b) providing sinusoidally varying amplitude signals for each of the two orthogonal axes, one of said sinusoidally varying amplitude signals being substantially 90° out of phase with the other;

(c) combining the sinusoidally varying reference signal with the sinusoidally varying amplitude signal for one axis to produce a drive signal for said one-axis; and (d) combining the sinusoidally varying reference signal with the sinusoidally varying amplitude signal for the other axis to produce a drive signal for the other axis.

* * * * *